US012558514B2

(12) United States Patent
Hanna et al.

(10) Patent No.: US 12,558,514 B2
(45) Date of Patent: Feb. 24, 2026

(54) DISCRETE FEMALE CATHETER

(71) Applicant: HR Pharmaceuticals, Inc., York, PA (US)

(72) Inventors: Matt Hanna, Lancaster, PA (US); Colby Wiesman, Wrightsville, PA (US); Chris Wiesman, York, PA (US); Randy Golden, Social Circle, GA (US); Sara Zebouni Miars, Bonita Springs, FL (US); John Golden, Greensboro, GA (US)

(73) Assignee: HR Pharmaceuticals, Inc., York, PA (US)

( * ) Notice: Subject to any disclaimer, the term of this patent is extended or adjusted under 35 U.S.C. 154(b) by 439 days.

(21) Appl. No.: 17/992,202

(22) Filed: Nov. 22, 2022

(65) Prior Publication Data

US 2024/0165372 A1     May 23, 2024

(51) Int. Cl.
*A61M 25/00* (2006.01)

(52) U.S. Cl.
CPC ...... *A61M 25/0017* (2013.01); *A61M 25/002* (2013.01)

(58) Field of Classification Search
CPC ............ A61M 25/0017; A61M 25/002; A61M 25/0111; A61M 2210/1089; A61M 2210/1092; A61M 1/87; A61M 25/0021; A61M 25/0043; A61M 2202/0496; A61M 25/013
See application file for complete search history.

(56) References Cited

U.S. PATENT DOCUMENTS

| | | | | |
|---|---|---|---|---|
| 3,854,483 | A | * 12/1974 | Powers | ............. A61M 25/0111 |
| | | | | 206/364 |
| 5,360,402 | A | * 11/1994 | Conway | ................. B29C 41/14 |
| | | | | 604/97.01 |
| 10,350,381 | B2 | 7/2019 | Schertiger et al. | |
| 2004/0158231 | A1* | 8/2004 | Tanghoj | ............ A61M 25/0067 |
| | | | | 604/544 |
| 2009/0008279 | A1* | 1/2009 | Tanghoej | ............ A61M 25/002 |
| | | | | 206/364 |
| 2009/0024111 | A1* | 1/2009 | Borodulin | ........... A61M 35/006 |
| | | | | 604/544 |
| 2009/0054876 | A1* | 2/2009 | Borodulin | ........... A61M 25/002 |
| | | | | 604/544 |

(Continued)

FOREIGN PATENT DOCUMENTS

| | | |
|---|---|---|
| AU | 2013382020 B2 | 9/2014 |
| EP | 1406690 B1 | 3/2005 |
| WO | 2022223984 A1 | 10/2022 |

OTHER PUBLICATIONS

Extended European Search Report, corresponding to EP Application No. 23211456.1-1122, dated May 15, 2024, 8 pages.

*Primary Examiner* — Adam Marcetich
(74) *Attorney, Agent, or Firm* — Barley Snyder

(57) ABSTRACT

A discrete catheter assembly as provided includes a containment unit and an outer protector layer. The outer protector layer has a rear cap, which is fitted over the shell base of the outer protector layer in which the front cap of the outer protector layer is removed while the rear cap of the outer protector layer is moved in a first direction away from the dispenser, then moved in a second direction to permit a movement of the catheter of the containment unit towards the dispenser.

19 Claims, 25 Drawing Sheets

(56) References Cited

U.S. PATENT DOCUMENTS

| | | | |
|---|---|---|---|
| 2009/0137986 A1* | 5/2009 | Golden | A61M 25/01 |
| | | | 220/735 |
| 2014/0194841 A1* | 7/2014 | Matthiassen | A61M 25/002 |
| | | | 604/328 |
| 2016/0193447 A1* | 7/2016 | Matthiassen | A61M 25/0136 |
| | | | 604/544 |
| 2019/0126004 A1 | 5/2019 | O'Brien et al. | |
| 2019/0358435 A1 | 11/2019 | Andersin et al. | |
| 2021/0100979 A1* | 4/2021 | Donnelly | A61M 25/0111 |
| 2021/0290893 A1* | 9/2021 | Palmer | A61M 27/00 |
| 2023/0072221 A1* | 3/2023 | Donnelly | A61M 25/002 |
| 2023/0364379 A1* | 11/2023 | Hughett, Sr. | A61M 25/002 |

* cited by examiner

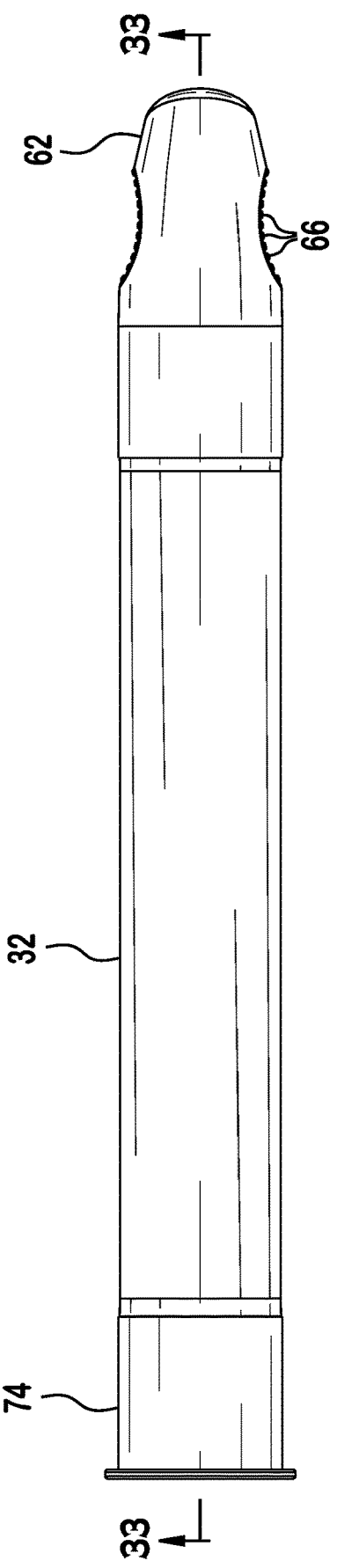
FIG. 31
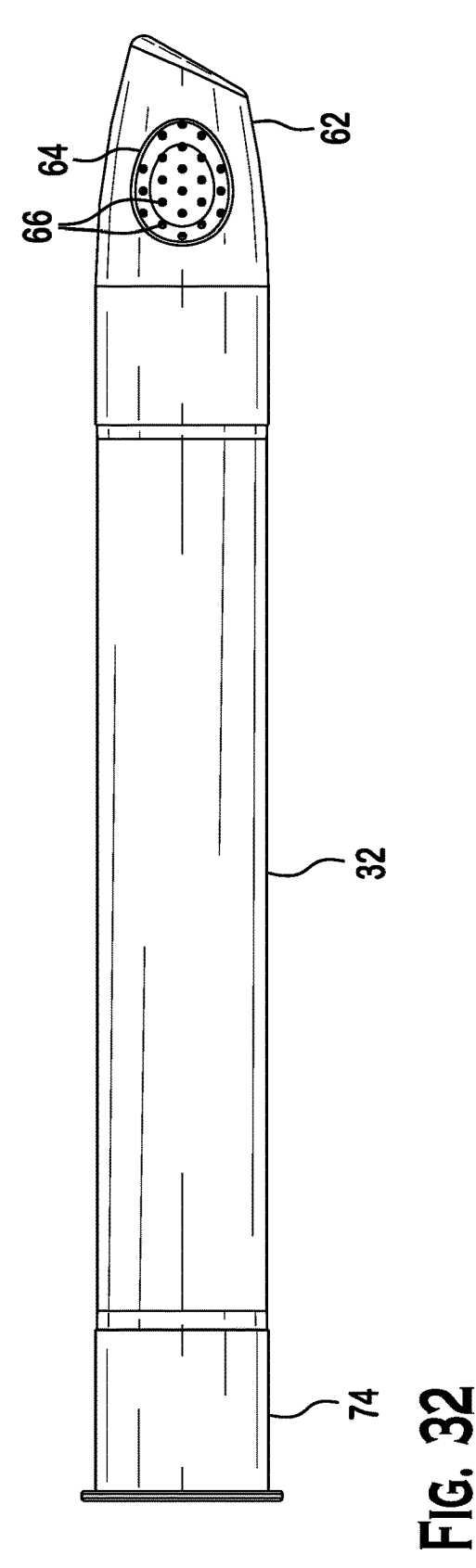
FIG. 32

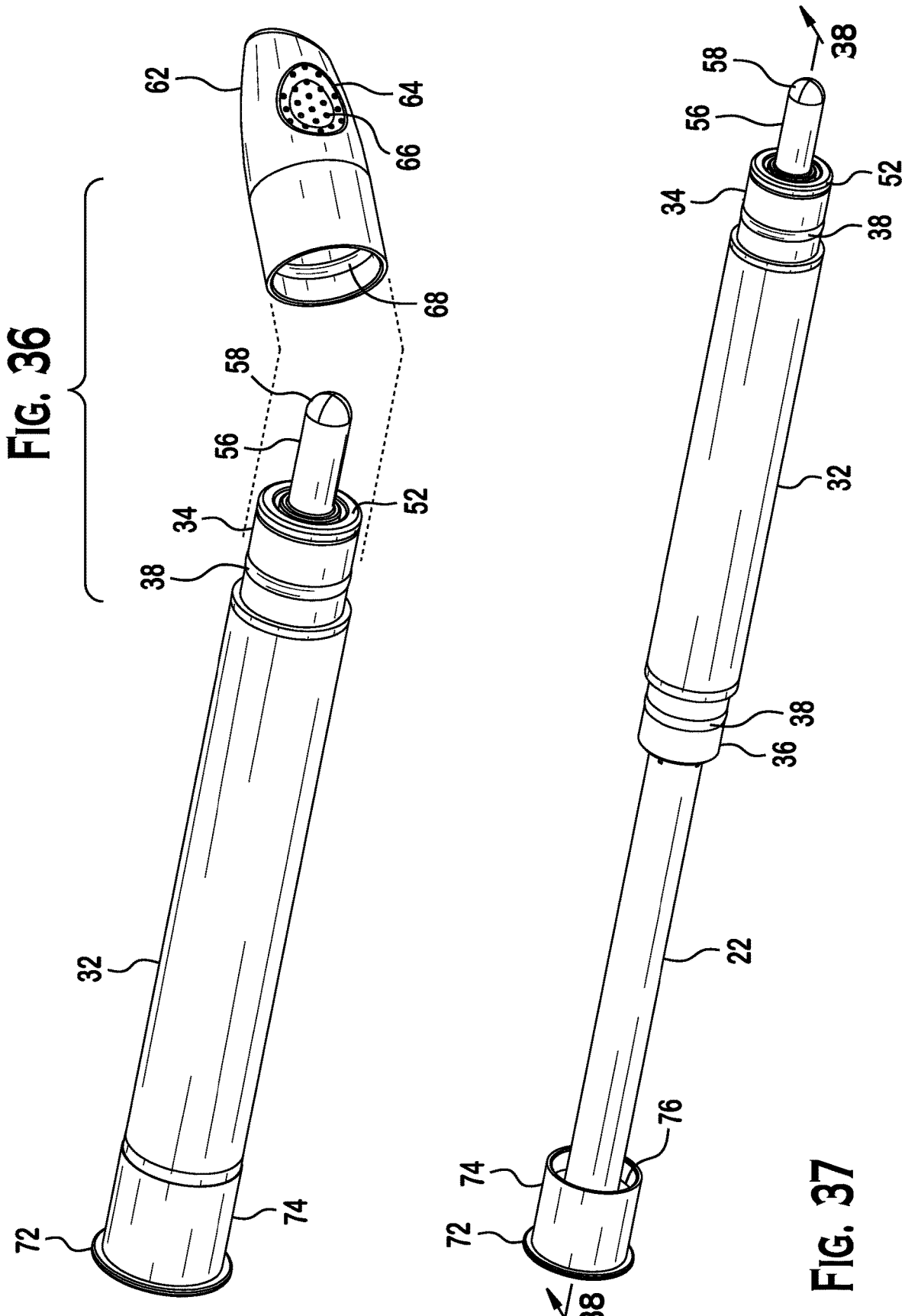

DISCRETE FEMALE CATHETER

FIELD OF THE INVENTION

The invention relates to a female catheter assembly and, more particularly, to a discrete female catheter assembly for fluid communication and release.

BACKGROUND

Catheters used in discretion to permit a user to administer self-catherization are known in the art. However, these discrete catheters also include the hassle of having the user twist and turn either a single component or a plurality of components in order to unlock and gain access to the catheter. Further, having the user physically remove the catheter from its container prior to self-catherization requires unnecessary effort. Moreover, the twisting and turning prolongs the time the user focuses on accessing the catheter while narrowing the time the user has in using the catheter if there is an emergency. In scenarios when the catheter is needed almost instantaneously, the known devices fail because of the added time needed to physically remove the catheter from its container prior to use.

Catheters for discrete use that allow a user to quickly access the catheter and administer self-catherization are preferably, light weight, easily accessible, allow for minimal clean up, and require minimal effort.

SUMMARY

A discrete catheter assembly as provided includes a containment unit having a holding vessel including a holding head member. The containment unit further having a catheter resting in an inner portion of the holding vessel and having a tube head positioned near the holding head member. The outer protector layer having a retainer having a first face and a second face. The outer protector layer further having a dispenser positioned adjacent to the first face of the retainer. The outer protector layer further having a shell enclosing the holding vessel in, which the shell further includes a shell head and a shell base. Moreover, the outer protector layer further having a front cap, which is fitted over the shell head. Lastly, the outer protector layer having a rear cap, which is fitted over the shell base in, which the front cap is removed while the rear cap is moved in a first direction away from the dispenser, then moved in a second direction to permit a movement of the catheter towards the dispenser.

BRIEF DESCRIPTION OF THE DRAWINGS

The invention will now be described by way of example with reference to the accompanying figures in which:

FIG. 31 is a top view of the invention of FIG. 30;

FIG. 32 is a right side view of the invention of FIG. 31

FIG. 36 is a top, front, right view of the invention of FIG. 35;

FIG. 37 is another perspective view of the invention of FIG. 36;

DETAILED DESCRIPTION OF THE EMBODIMENT(S)

Figure 1:
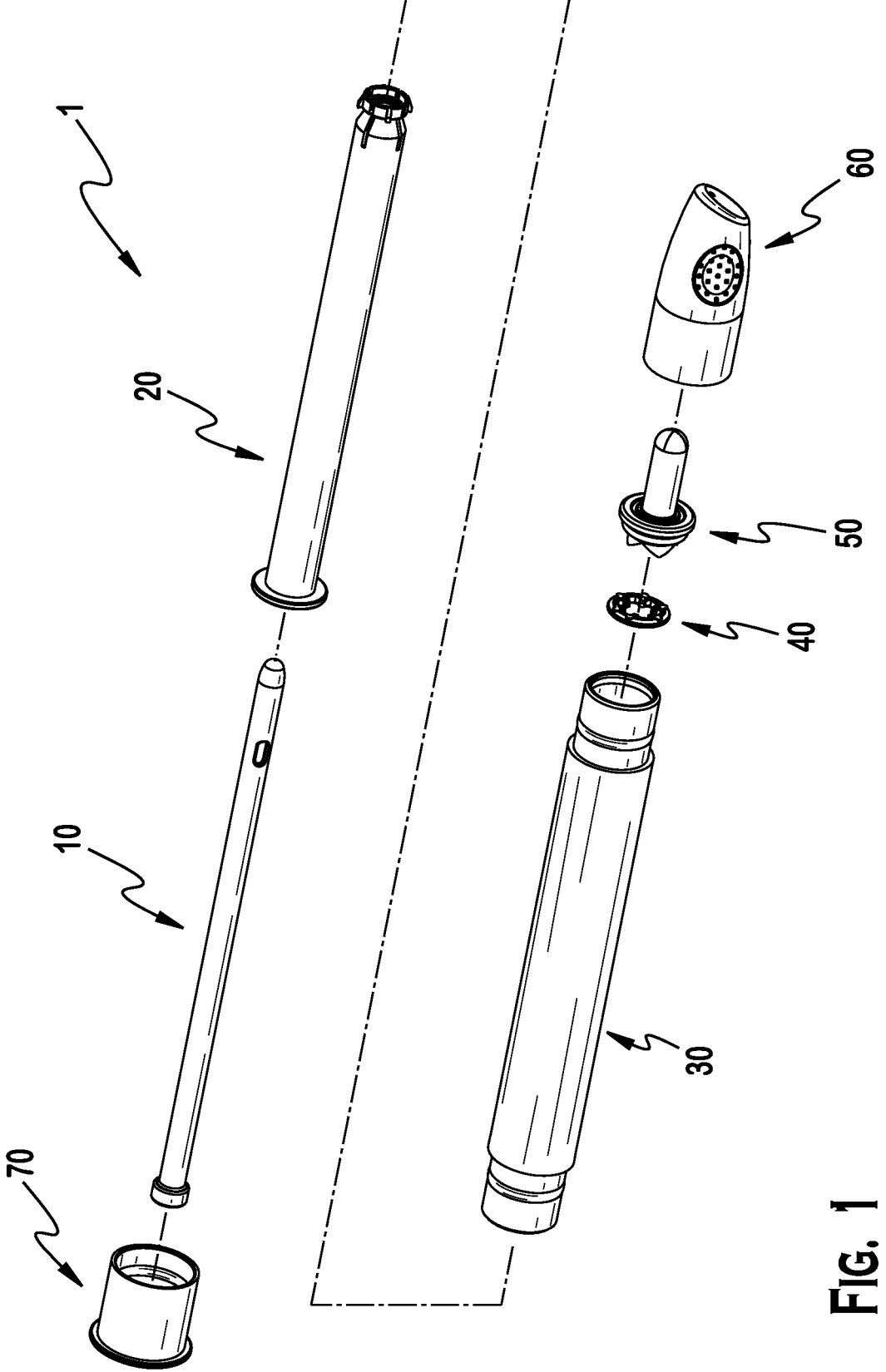
FIG. 1 is an exploded view of the discrete catheter assembly.

With reference to a shown exemplary embodiment, a discrete catheter assembly 1 according to the invention is generally constructed with the following major components: a containment unit and an outer protector layer as shown through-out and specifically in FIG. 1.

In the exemplary embodiment, the containment unit generally includes a catheter 10 and a holding vessel 20. One of ordinary skill in the art would understand the applicant's design is not the exclusive embodiment. Rather, more or less features may be added or withdrawn within the spirit of the invention.

Figures 2, 3, 4, 5:
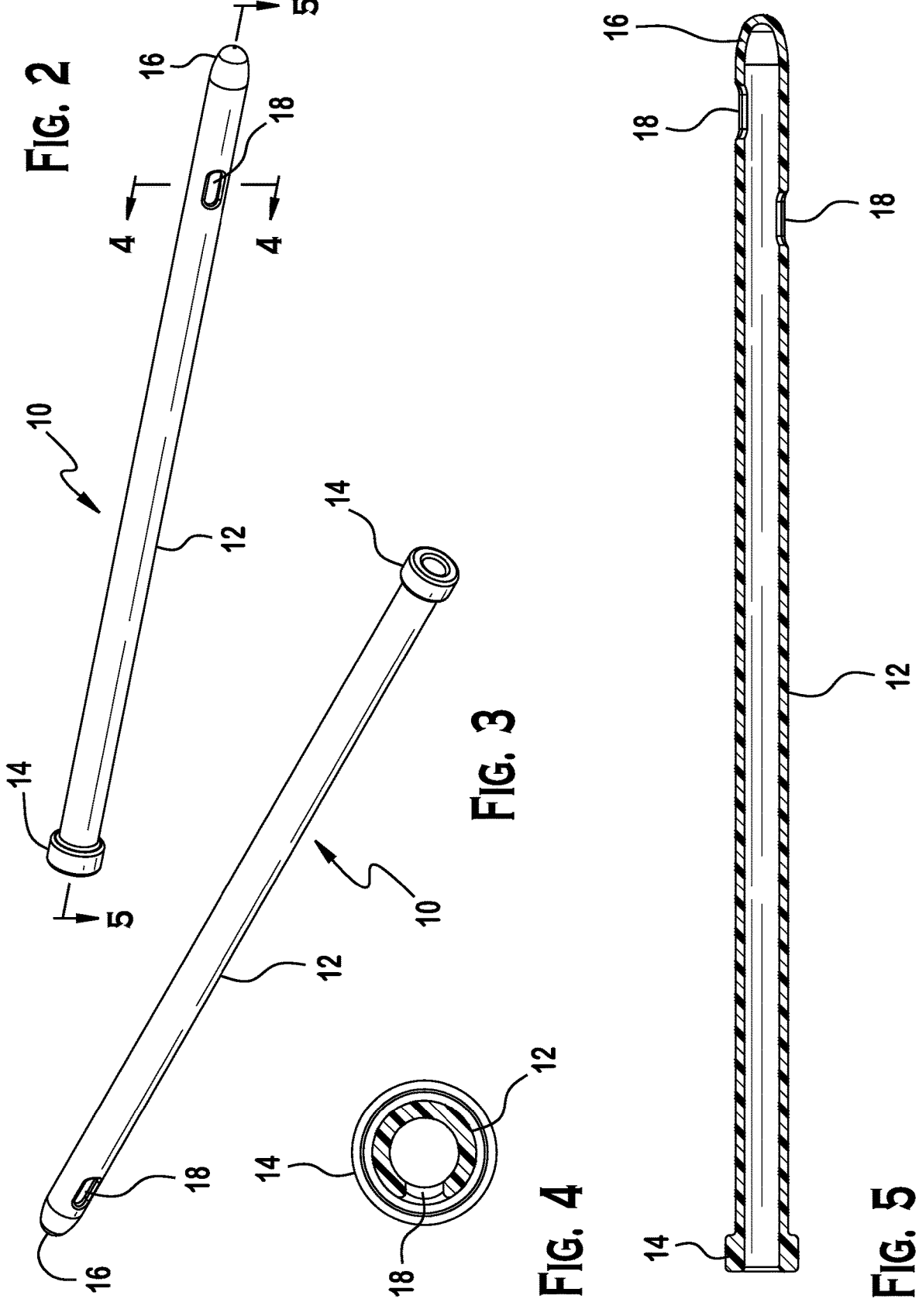
FIG. 2 is a top, front, right view of the invention in FIG. 1.
FIG. 3 is a top, rear, left view of the invention in FIG. 2.
FIG. 4 is a cross-sectional view of the invention of FIG. 3.
FIG. 5 is a top cross-sectional view of the invention of FIG. 4.
Figures 6, 7, 8:
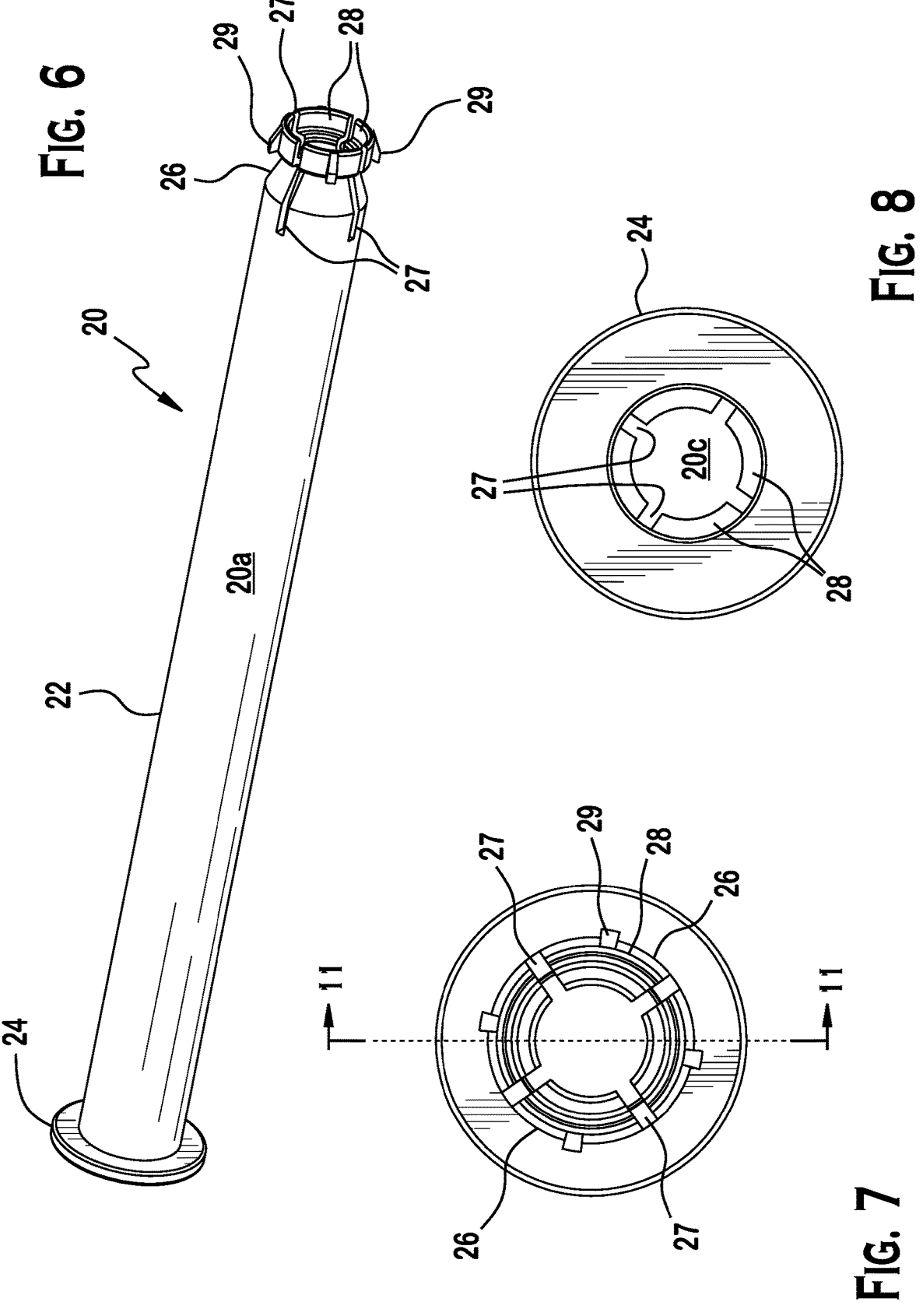
FIG. 6 is a top, front, right view of the invention of FIG. 5.
FIG. 7 is a top view of the invention of FIG. 6.
FIG. 8 is a top view of the invention of FIG. 7.

In the exemplary embodiment, as shown in FIGS. 1-5, the catheter 10 is generally composed of a tube body 12. One of ordinary skill in the art would understand the applicant's design is not the exclusive embodiment. In the exemplary embodiment, the tube body 12 is an elongated member. One of ordinary skill in the art would understand the applicant's design is not the exclusive embodiment. In the exemplary embodiment, the catheter 10 further includes a base 14, as shown a projecting base 14, which is located at the lower end of the tube body 12. One of ordinary skill in the art would understand the applicant's design is not the exclusive embodiment. The projecting base 14 is a circular outdent with a circumference greater than the circumference of the tube body 12 as shown in FIGS. 2-3. One of ordinary skill in the art would understand the applicant's design is not the exclusive embodiment.

In the exemplary embodiment, the catheter 10 further includes a tube head 16. The tube head 16 is a rounded conical top member. One of ordinary skill in the art would understand the applicant's design is not the exclusive embodiment.

In the exemplary embodiment, the catheter 10 further includes eye slits 18 located near the tube head 16. One of ordinary skill in the art would understand the applicant's design is not the exclusive embodiment.

In the exemplary embodiment, the catheter 10 further includes a tube passageway beginning near the projecting base 14 and extending the length of the catheter 10. One of ordinary skill in the art would understand the applicant's design is not the exclusive embodiment. Moreover, the tube passageway is lined with a hydrophilic coating. One of ordinary skill in the art would understand the applicant's design is not the exclusive embodiment.

In the exemplary embodiment, the holding vessel 20 is generally constructed with the following: a holding body member 22, a holding base member 24, and a holding head member 26 as shown in FIG. 6-11.

In the exemplary embodiment, shown in FIGS. 6-11, the holding vessel 20 includes an outer face 20a, an inner face 20b and a holding vessel passageway 20c, which extends the length of the holding vessel 20. One of ordinary skill in the art would understand the applicant's design is not the exclusive embodiment.

In the exemplary embodiment, the holding body member 22 is an elongated cylinder. One of ordinary skill in the art would understand the applicant's design is not the exclusive embodiment.

In the exemplary embodiment, as shown, the holding base member 24 is a circular disk protruding from a rear of the holding vessel 20. One of ordinary skill in the art would understand the applicant's design is not the exclusive embodiment.

Figures 9, 10:
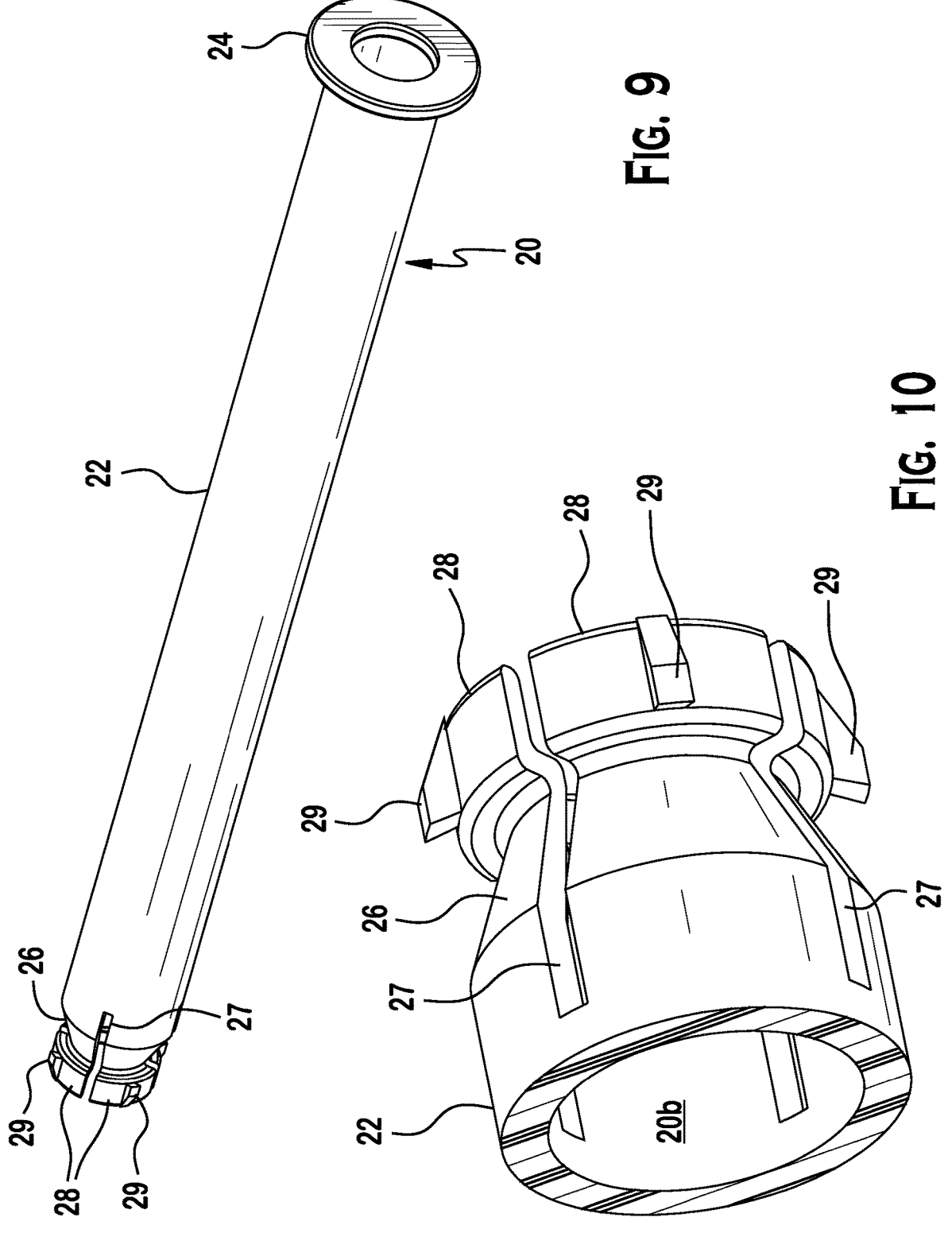
FIG. 9 is a top, rear, left view of the invention of FIG. 8.
FIG. 10 is an enlarged view of the invention of FIG. 9.
Figure 11:
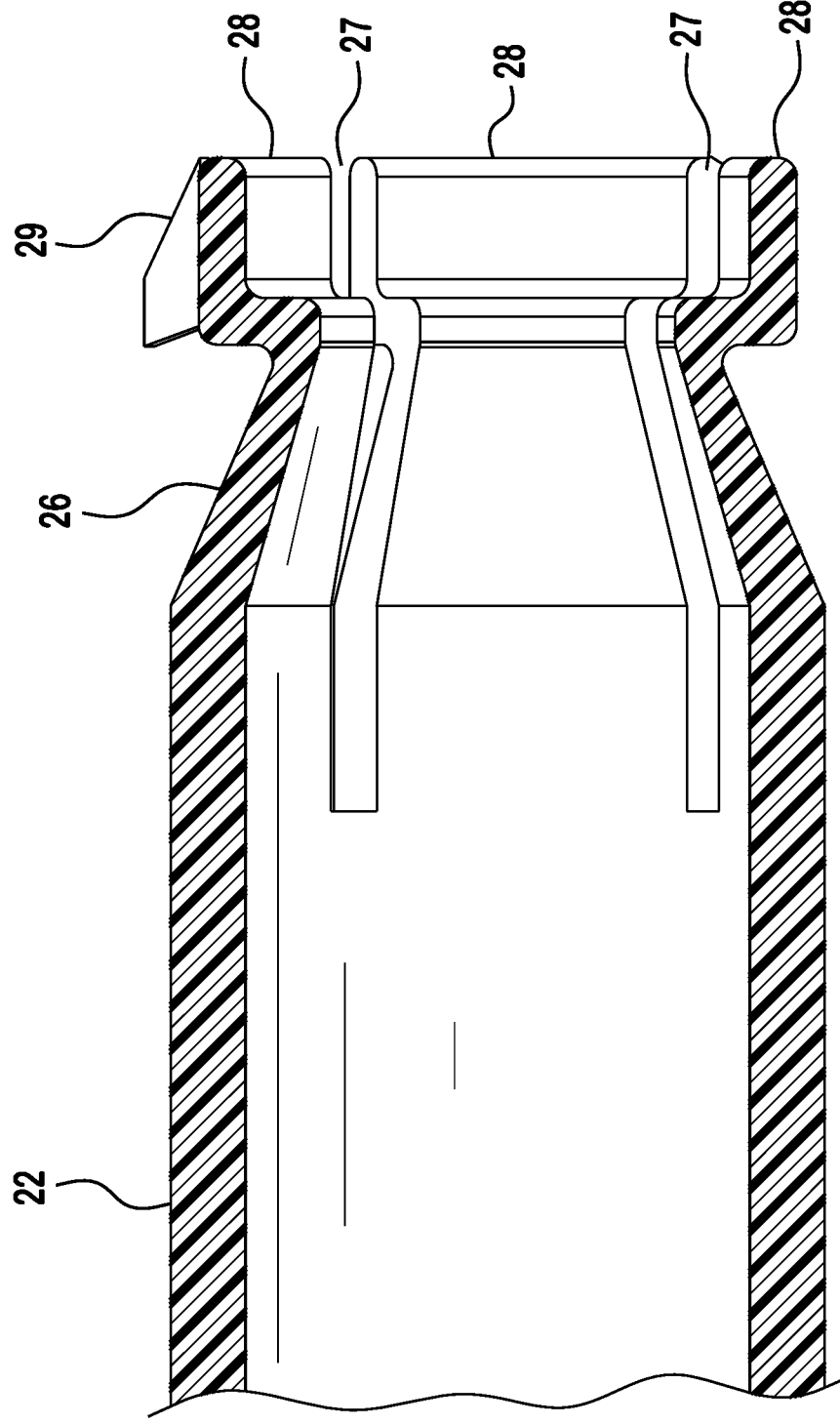
FIG. 11 is another enlarged view of the invention of FIG. 10.
Figures 12, 13, 14:
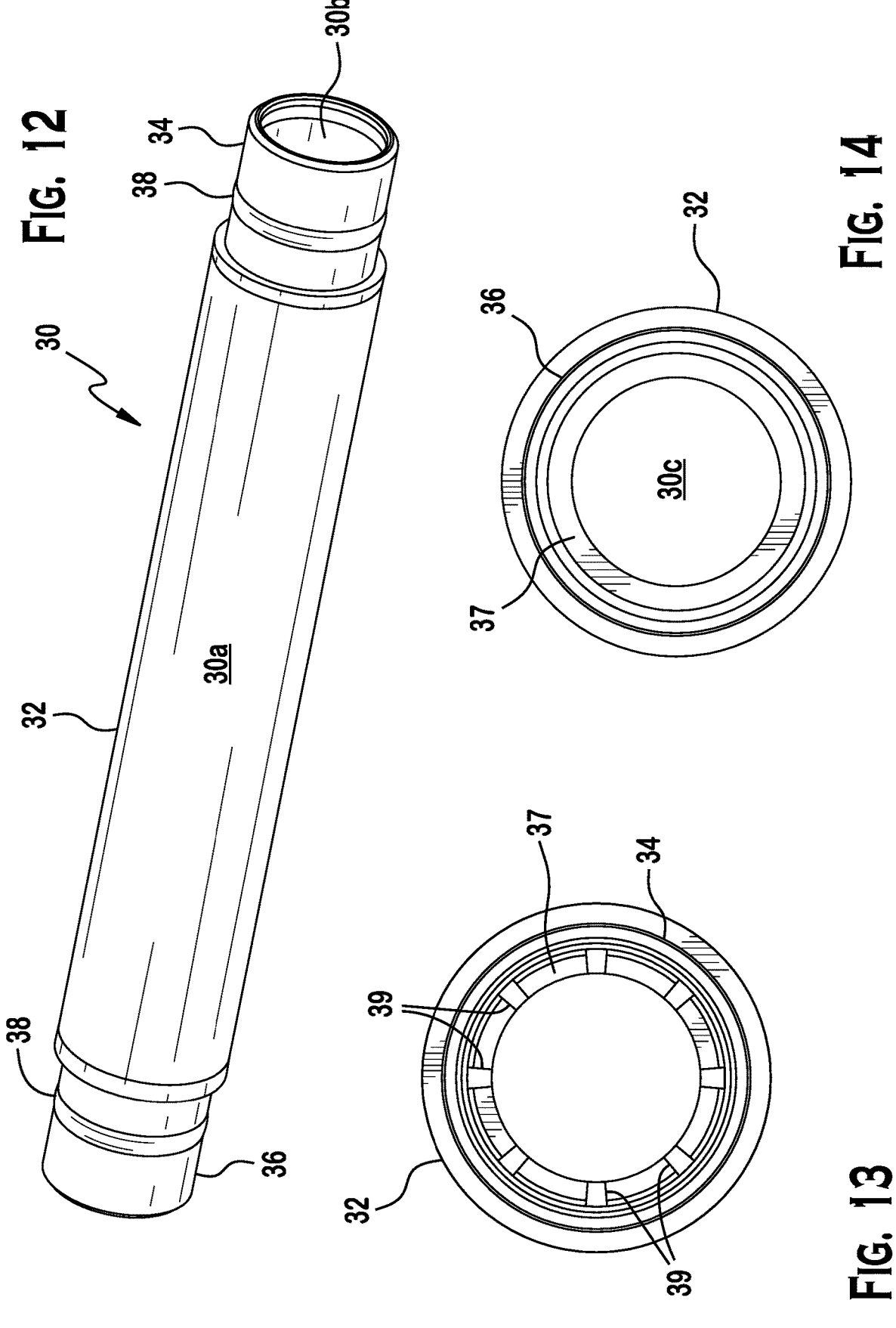
FIG. 12 is a top, front, right view of the invention of FIG. 11.
FIG. 13 is a top view of the invention of FIG. 12.
FIG. 14 is a rear view of the invention of FIG. 13.
Figures 15, 16:
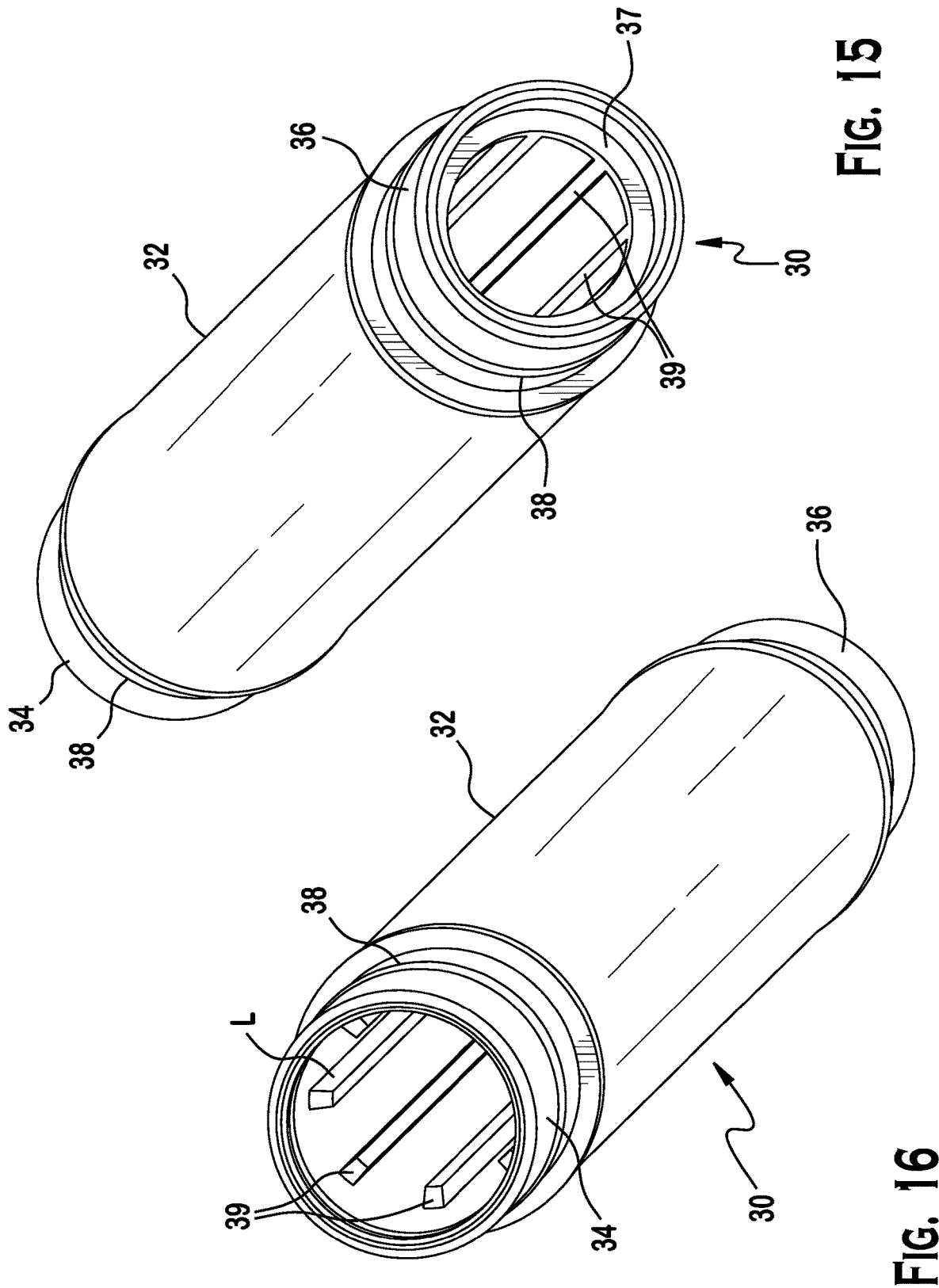
FIG. 15 is a top, rear left view of the invention of FIG. 14.
FIG. 16 is a top, front, right view of the invention of FIG. 15.

In the exemplary embodiment, as shown in FIGS. 10-11, the holding head member 26 is frustrum shaped. One of ordinary skill in the art would understand the applicant's design is not the exclusive embodiment.

In the exemplary embodiment, the holding head member 26 further includes a raised circular ring 25 located on the inner face 20b of the holding head member 26.

In the exemplary embodiment, the holding head member 26 further includes a plurality of slits 27 located at four points on the outer face 20a of holding head member 26. One of ordinary skill in the art would understand the applicant's design is not the exclusive embodiment. The slits 27 are elongated gaps running the length of the holding head member 26.

In the exemplary embodiment, holding head member 26 further includes a circular cradle 28 located at the top of the holding vessel 20. In the exemplary embodiment, the holding head member 26 further includes a plurality of flaps 29 located on the outer face 20a of the circular cradle 28. One of ordinary skill in the art would understand the applicant's design is not the exclusive embodiment. In the exemplary embodiment, the flaps 29 are quadrilateral shaped. More particularly, the flaps 29 are trapezoidal shaped. One of ordinary skill in the art would understand the applicant's design is not the exclusive embodiment.

In the exemplary embodiment, an outer protector layer according to the invention is generally constructed with the following: a shell 30, a retainer 40, a dispenser 50, a front cap 60 and a rear cap 70.

In an exemplary embodiment, as shown in FIGS. 12-16, the shell 30 is mainly composed of a shell body 32, a shell head 34 and a shell base 36. One of ordinary skill in the art would understand the applicant's design is not the exclusive embodiment. In the exemplary embodiment, the shell 30 further includes an outer face 30a and an inner face 30b. The shell 30 further includes a shell passageway 30c extending the length of the shell 30.

In the exemplary embodiment, the shell body 32 is an elongated cylindrical member. One of ordinary skill in the art would understand the applicant's design is not the exclusive embodiment.

In the exemplary embodiment, the shell head 34 is a cylindrical member. The shell head 34 includes a smaller circumference than a circumference of the shell body 32. One of ordinary skill in the art would understand the applicant's design is not the exclusive embodiment.

In the exemplary embodiment, the shell base 36 is a cylindrical member. One of ordinary skill in the art would understand the applicant's design is not the exclusive embodiment. In the exemplary embodiment, the shell base 36 includes a smaller circumference than the circumference of the shell body 32. One of ordinary skill in the art would understand the applicant's design is not the exclusive embodiment.

In the exemplary embodiment, the shell base 36 further includes a free-floating circular ring 37 located on the inner face 30b of the shell base 36. One of ordinary skill in the art would understand the applicant's design is not the exclusive embodiment. In the exemplary embodiment, the shell base 36 also includes the raised groove 38 located around the circumference of the shell base 36. One of ordinary skill in the art would understand the applicant's design is not the exclusive embodiment.

In the exemplary embodiment, the shell 30 further includes a plurality of rectangular protrusions 39 located on the inner face 30b. The rectangular protrusions 39 extend the length of the shell 30 and are attached to the free-floating circular ring 37. One of ordinary skill in the art would understand the applicant's design is not the exclusive embodiment. Moreover, the plurality of rectangular protrusions 39 include a ledge L. The ledge L is formed by the holding vessel 20 and the rectangular protrusions 39. One of ordinary skill in the art would understand the applicant's design is not the exclusive embodiment.

Figures 17, 18:
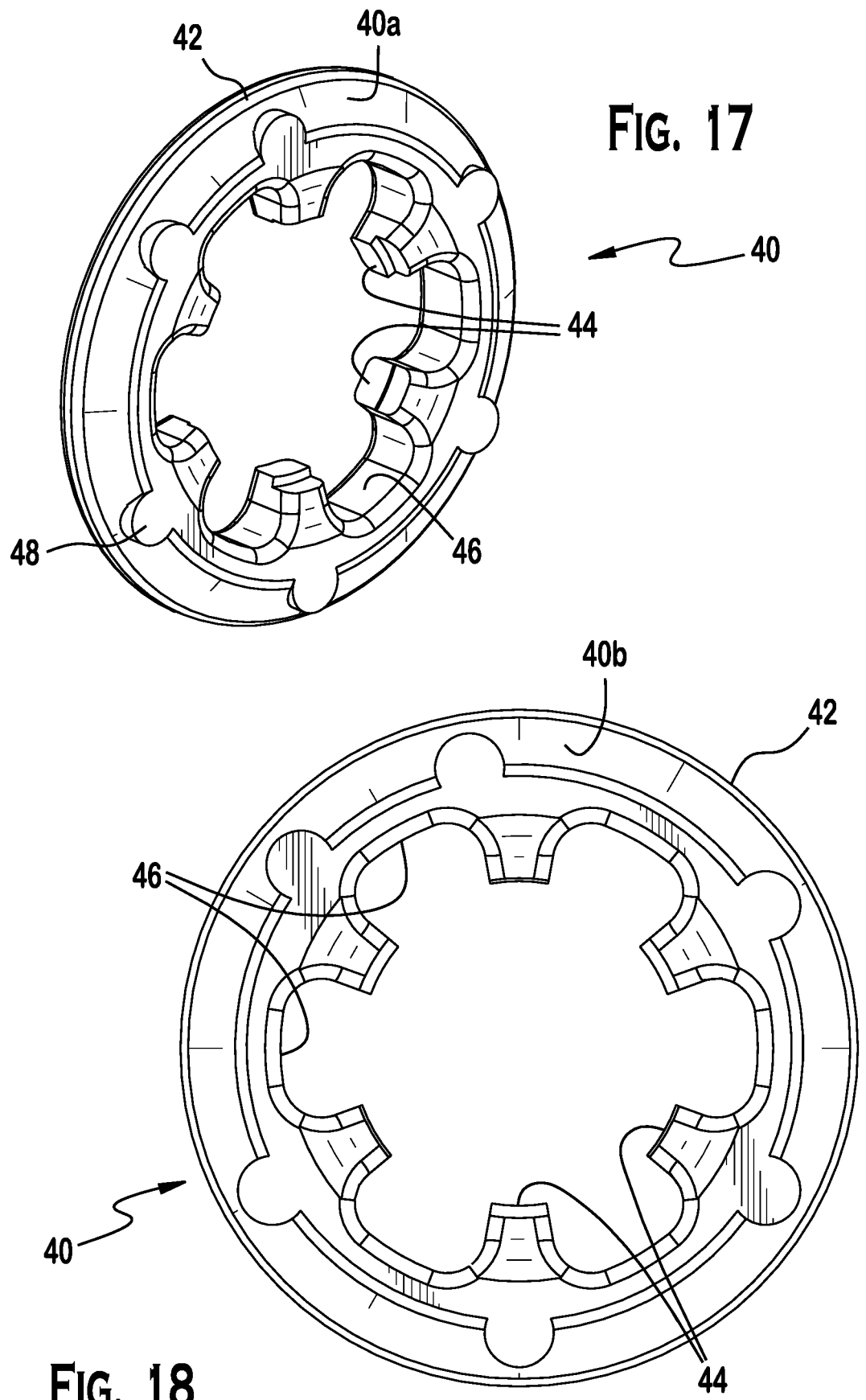
FIG. 17 is a top, front, right view of the invention of FIG. 16.
FIG. 18 is a front view of the invention of FIG. 17.
Figures 19, 20:
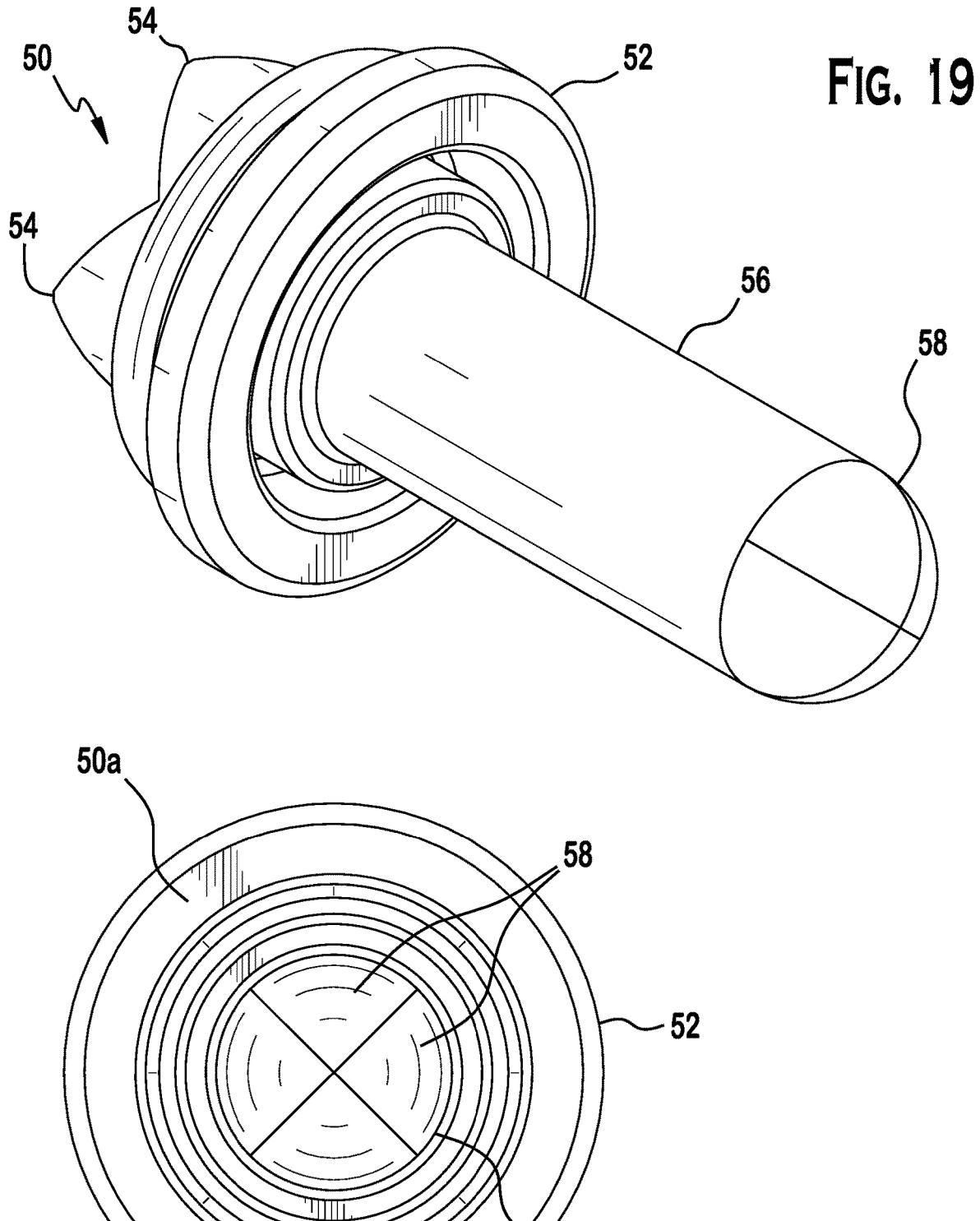
FIG. 19 is a top, front, right view of the invention of FIG. 18.
FIG. 20 is a front view of the invention of FIG. 19.
Figures 21, 22:
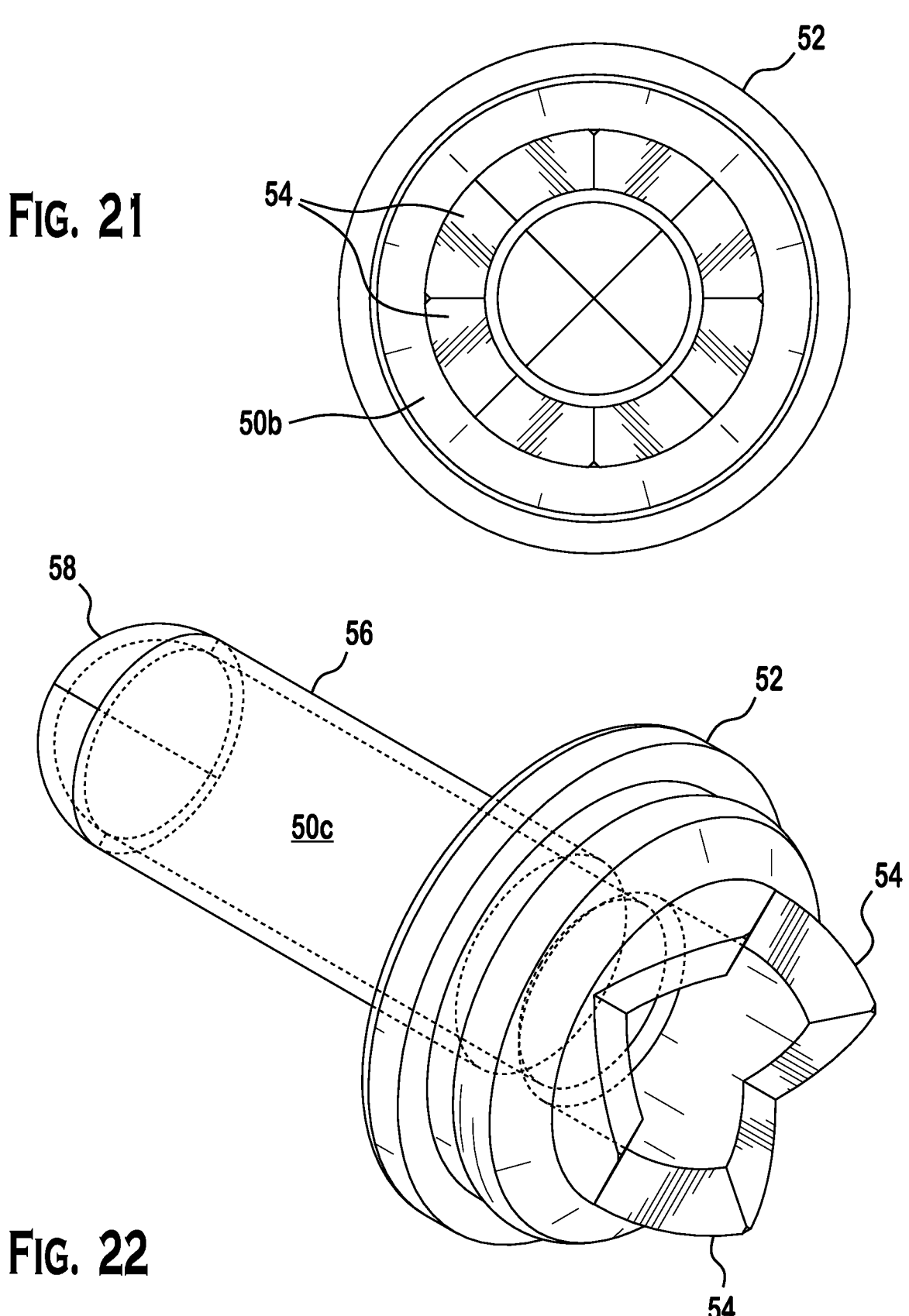
FIG. 21 is a rear view of the invention of FIG. 20.
FIG. 22 is a top, rear, left view of the invention of FIG. 21.

In the exemplary embodiment, as shown in FIGS. 17-18, the retainer 40 is generally composed of a ring member 42. One of ordinary skill in the art would understand the applicant's design is not the exclusive embodiment. In the exemplary embodiment, the retainer 40 further includes a first face 40a and a second face 40b on the ring member 42. One of ordinary skill in the art would understand the applicant's design is not the exclusive embodiment.

In the exemplary embodiment, the retainer 40 further includes a retainer opening located in the center of the ring member 42. One of ordinary skill in the art would understand the applicant's design is not the exclusive embodiment.

In the exemplary embodiment, the retainer 40 further includes a plurality of teeth-like protrusions 44 extending inwards towards the retainer opening. One of ordinary skill in the art would understand the applicant's design is not the exclusive embodiment.

In the exemplary embodiment, the retainer 40 further includes a plurality of retainer indentations 46 located between each teeth-like protrusion 44 extending away from the retainer opening. One of ordinary skill in the art would understand the applicant's design is not the exclusive embodiment.

In the exemplary embodiment, the retainer 40 further includes a plurality of circular protrusions 48 located on both the first face 40a and the second face 40b of the ring member 42. One of ordinary skill in the art would understand the applicant's design is not the exclusive embodiment.

In the exemplary embodiment, as shown in FIGS. 19-22, the dispenser 50 is mainly composed of a tip base 52, a biasing surface 54 and a protruding end piece 56. One of ordinary skill in the art would understand the applicant's design is not the exclusive embodiment.

The dispenser 50 further includes a front face 50a and a rear face 50b. The dispenser also includes a dispenser passageway 50c running the length of the dispenser 50. One of ordinary skill in the art would understand the applicant's design is not the exclusive embodiment.

In the exemplary embodiment, the tip base 52 is a shortened cylindrical member. One of ordinary skill in the art would understand the applicant's design is not the exclusive embodiment.

In the exemplary embodiment, the biasing surface 54 is a protruding wall positioned on the rear face 50b extending outward. One of ordinary skill in the art would understand the applicant's design is not the exclusive embodiment.

In the exemplary embodiment, the protruding end piece 56 is positioned on the front face 50a extending outwards from the tip base 52. One of ordinary skill in the art would understand the applicant's design is not the exclusive embodiment. In the exemplary embodiment, the protruding end piece 56 further includes a distal tip 58. One of ordinary skill in the art would understand the applicant's design is not the exclusive embodiment.

In the exemplary embodiment, the distal tip 58 further includes an "X shaped" opening. One of ordinary skill in the art would understand the applicant's design is not the exclusive embodiment.

Figures 23, 24, 25:
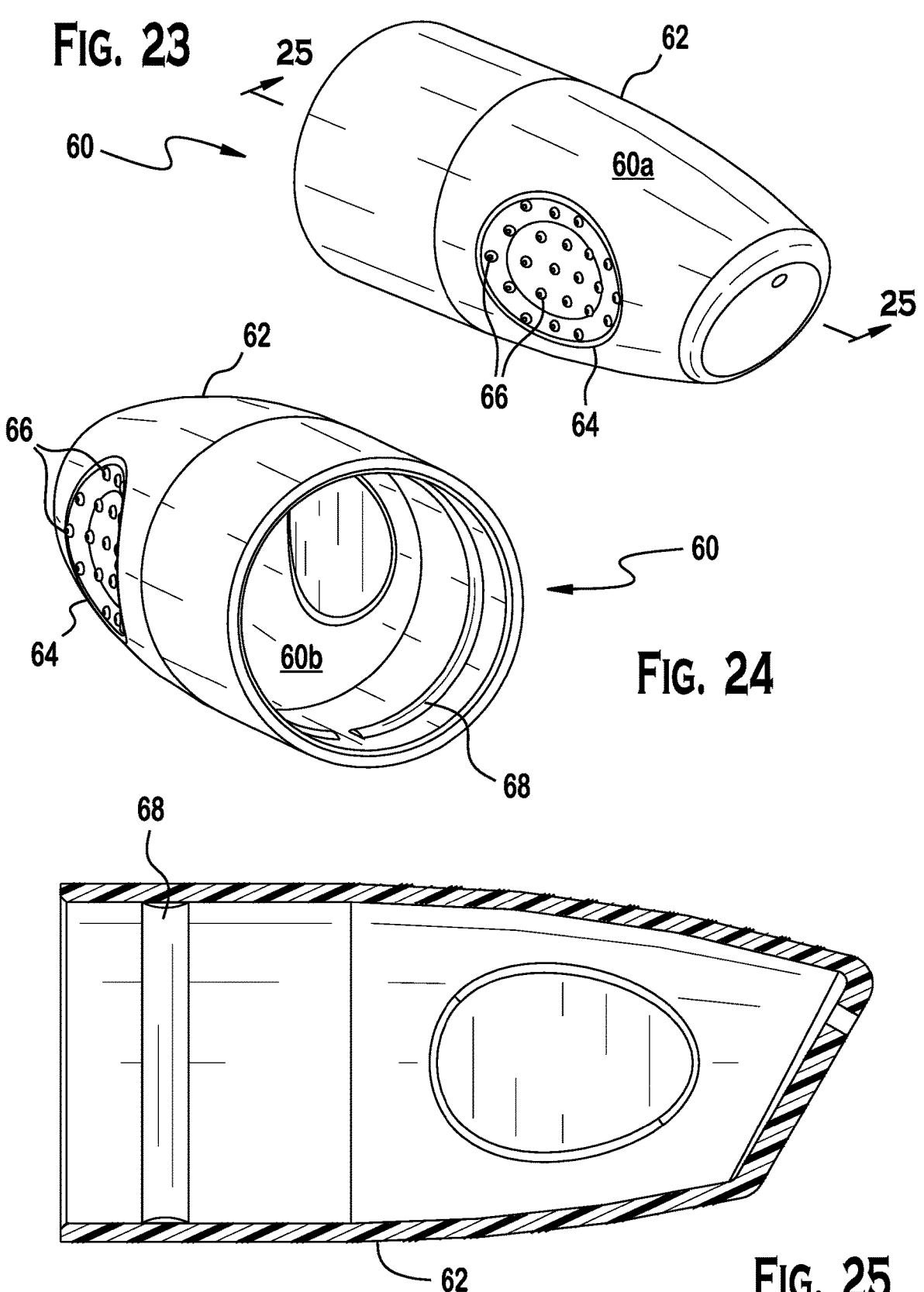
FIG. 23 is a top, front, right view of the invention of FIG. 22.
FIG. 24 is a top, rear, left view of the invention of FIG. 23.
FIG. 25 is a right view of the invention of FIG. 24.

In the exemplary embodiment, as shown in FIGS. 23-25, the front cap 60 is an elongated member 62. One of ordinary skill in the art would understand the applicant's design is not the exclusive embodiment. The front cap 60 further includes an outer face 60a and an inner face 60b. In the exemplary embodiment, the front cap 60 further includes a circular indentation 64 located on parallel sides of the front cap 60. One of ordinary skill in the art would understand the applicant's design is not the exclusive embodiment.

In the exemplary embodiment, the circular indentation 64 further includes a plurality of raised circular outdents 66. One of ordinary skill in the art would understand the applicant's design is not the exclusive embodiment. In the exemplary embodiment, the front cap 60 further includes a front cap air release passageway located on the top of the inclined head of the elongated member 62. One of ordinary skill in the art would understand the applicant's design is not the exclusive embodiment.

In the exemplary embodiment, the front cap 60 further includes a circular groove 68 extending the full circumference and located on the inner face 60b of the elongated member 62. One of ordinary skill in the art would understand the applicant's design is not the exclusive embodiment.

Figures 26, 27, 28:
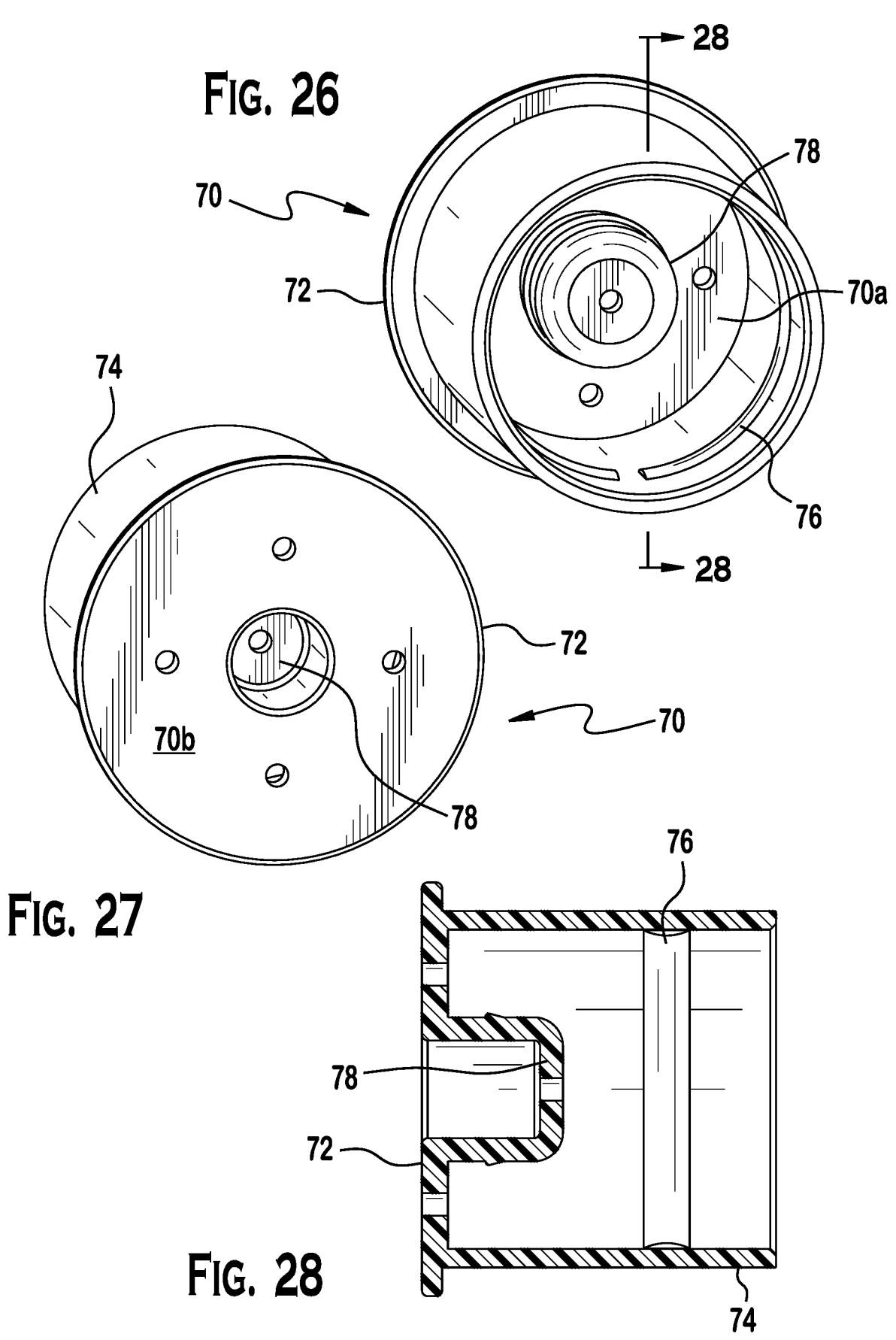
FIG. 26 is a top, front, right view of the invention of FIG. 25.
FIG. 27 is a top, rear, left view of the invention of FIG. 26.
FIG. 28 is a right view of the invention of FIG. 27.
Figures 29, 30:
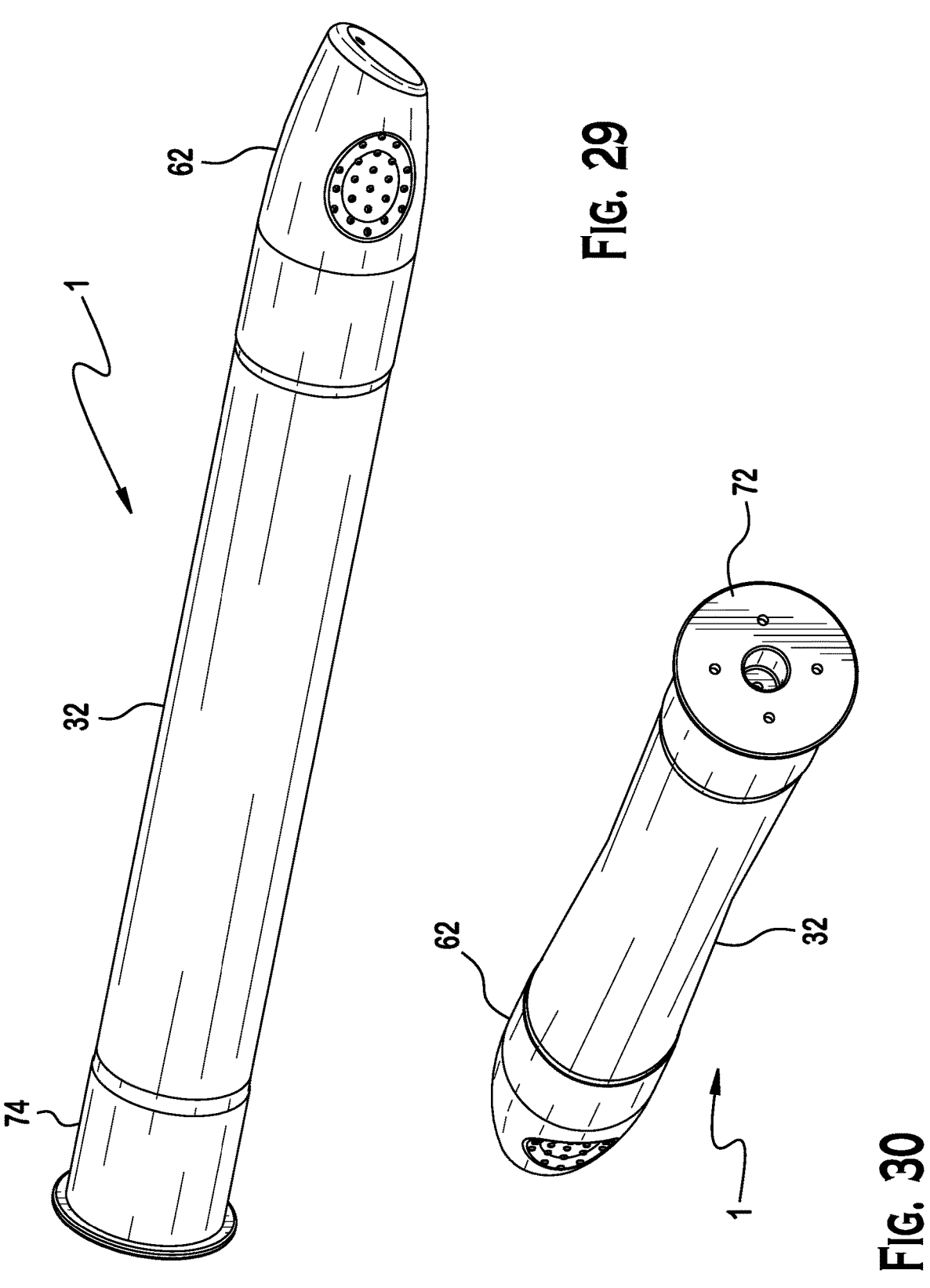
FIG. 29 is a top, front, right view of the invention of FIG. 28.
FIG. 30 is a top, rear, left view of the invention of FIG. 29.
Figure 33:
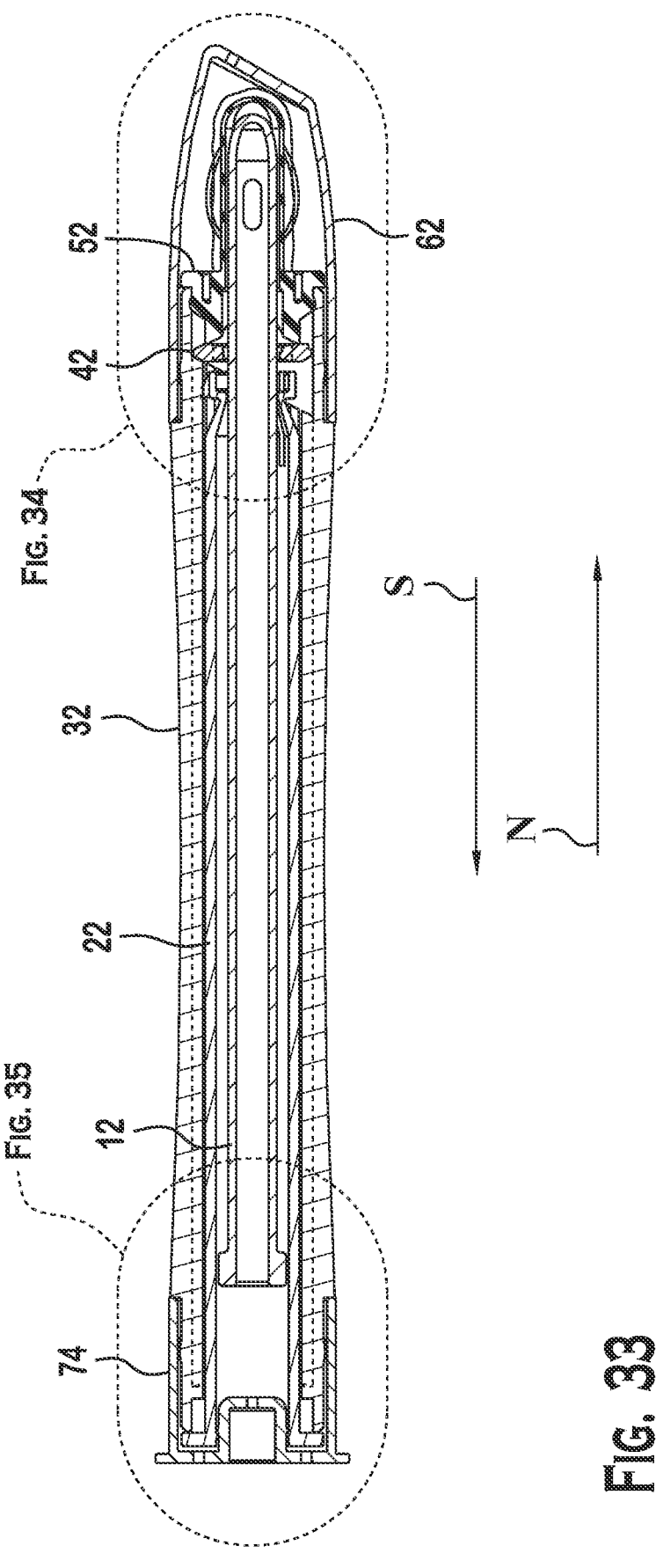
FIG. 33 is a cross sectional view of the invention of FIG. 32.
Figures 34, 35:
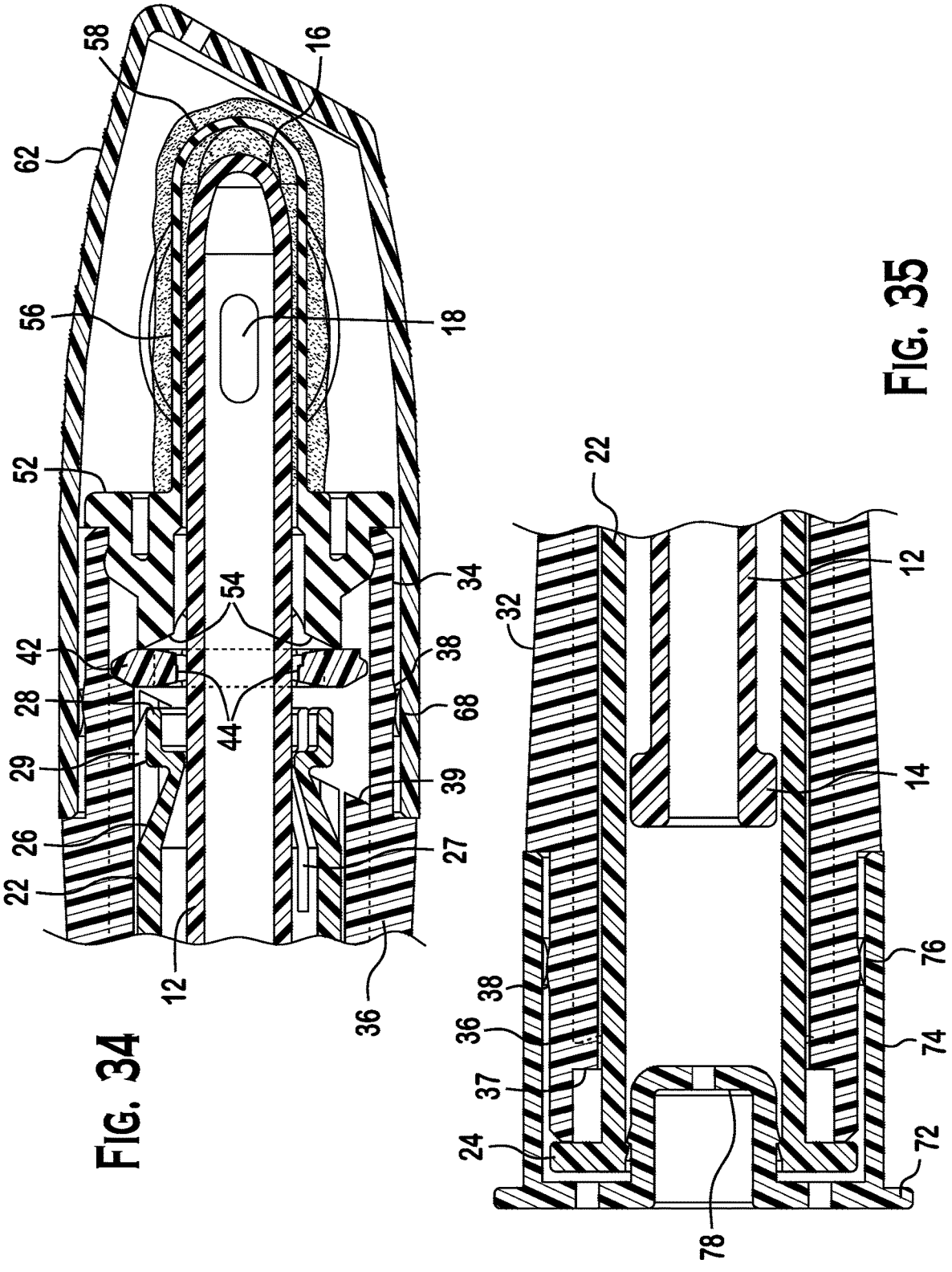
FIG. 34 is an enlarged view of the invention of FIG. 33.
FIG. 35 is an enlarged view of the invention of FIG. 34
Figures 38, 39:
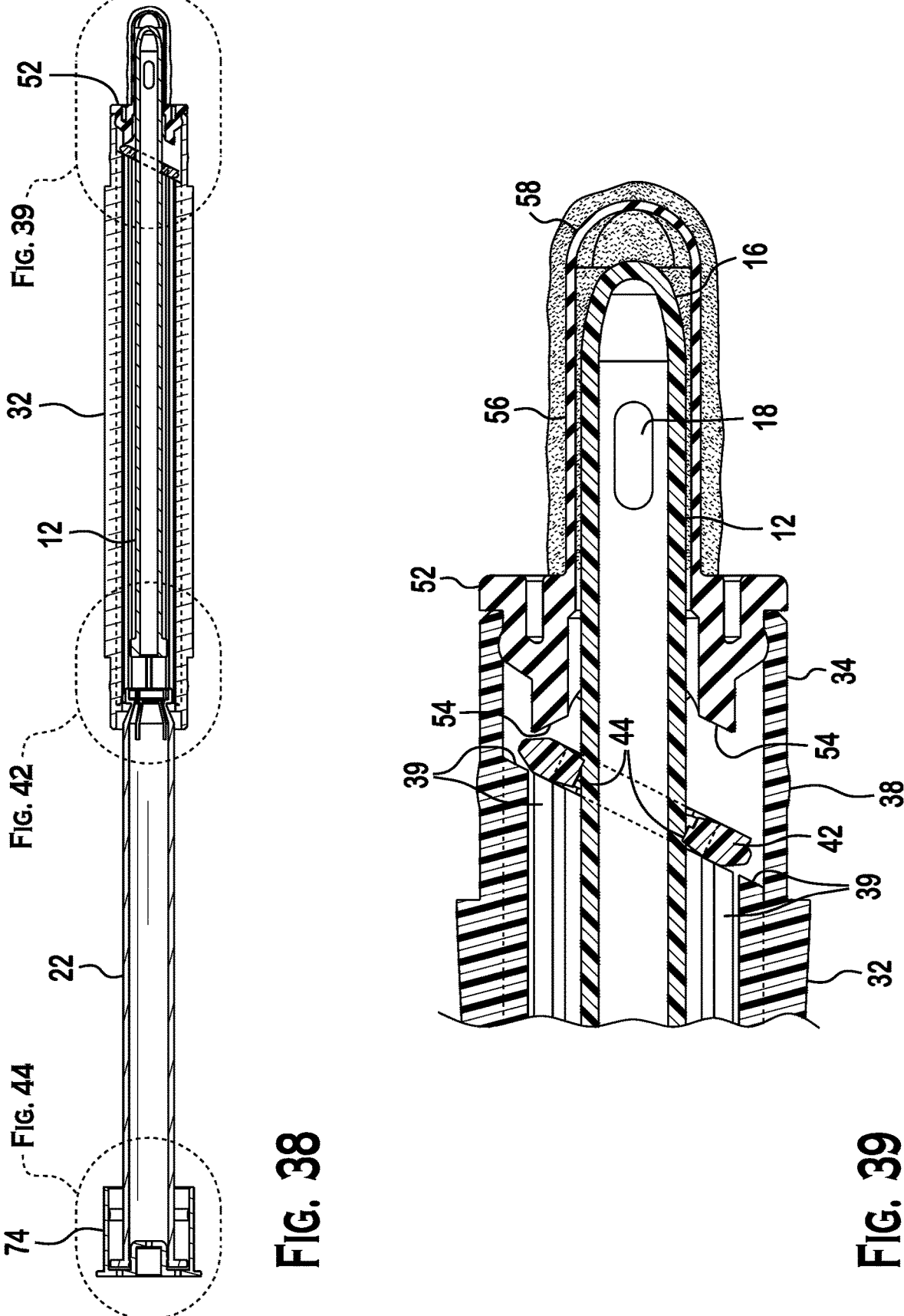
FIG. 38 is a cross sectional view of the invention of FIG. 37.
FIG. 39 is another cross sectional view of the invention of FIG. 38.
Figures 40, 41:
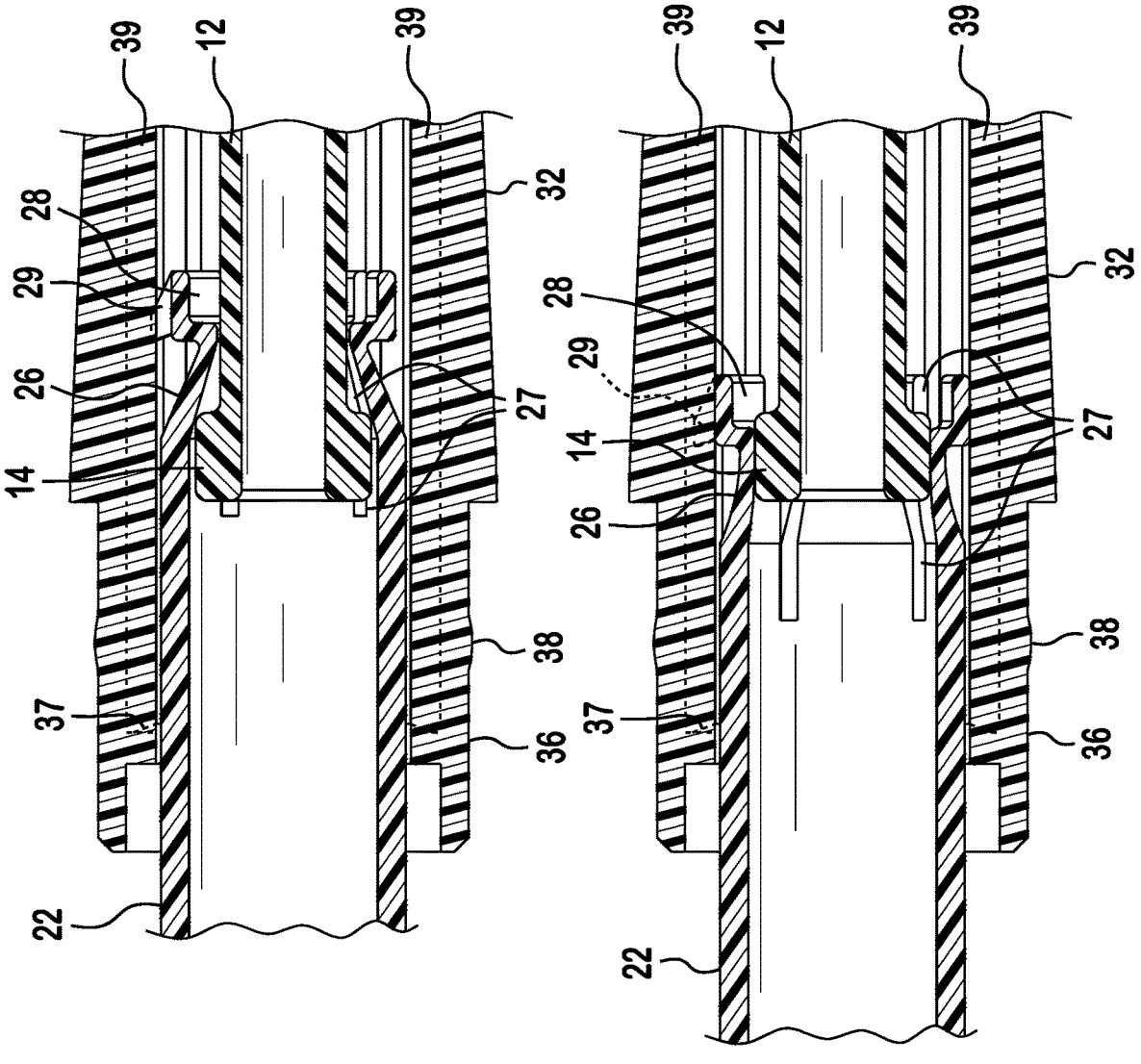
FIG. 40 is another cross sectional view of the invention of FIG. 39.
FIG. 41 is another cross sectional view of the invention of FIG. 40.
Figures 42, 43:
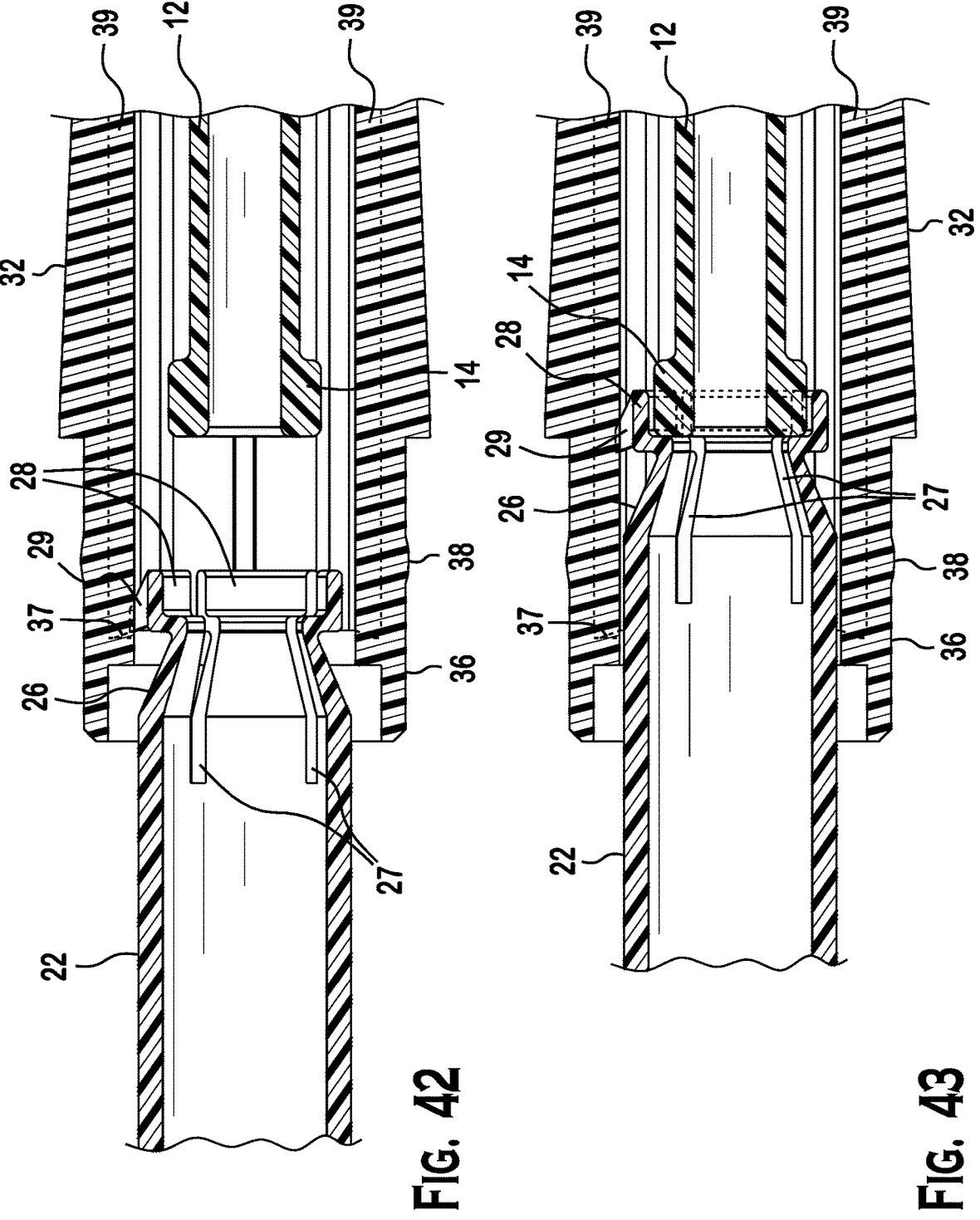
FIG. 42 is another cross sectional view of the invention of FIG. 41.
FIG. 43 is another cross sectional view of the invention of FIG. 42.
Figure 44:
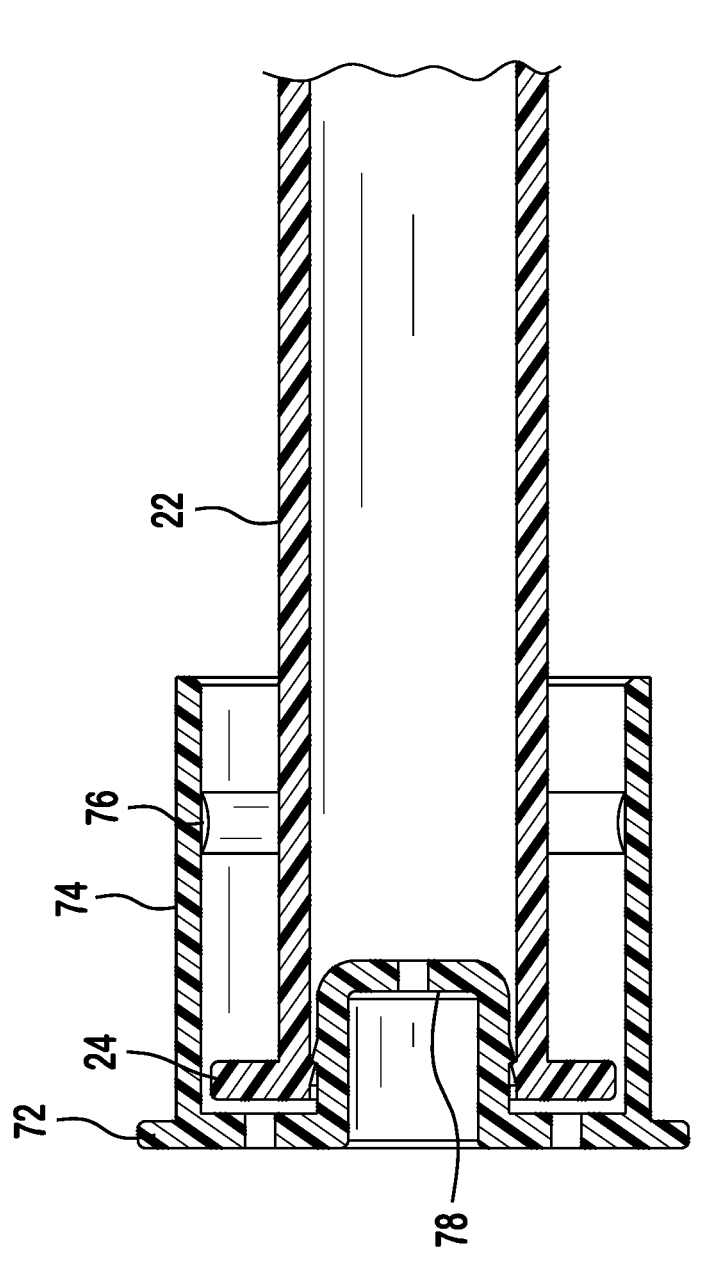
FIG. 44 is another cross sectional view of the invention of FIG. 43.
Figure 45:
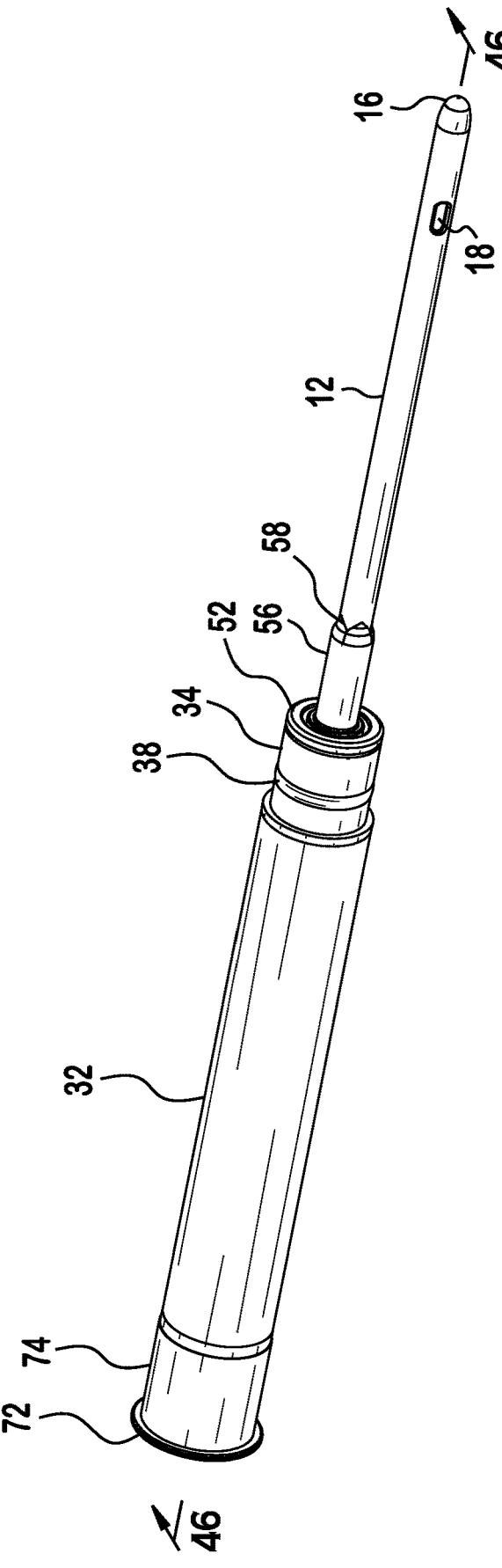
FIG. 45 is a top, front, right view of the invention of FIG. 44.
Figure 46:
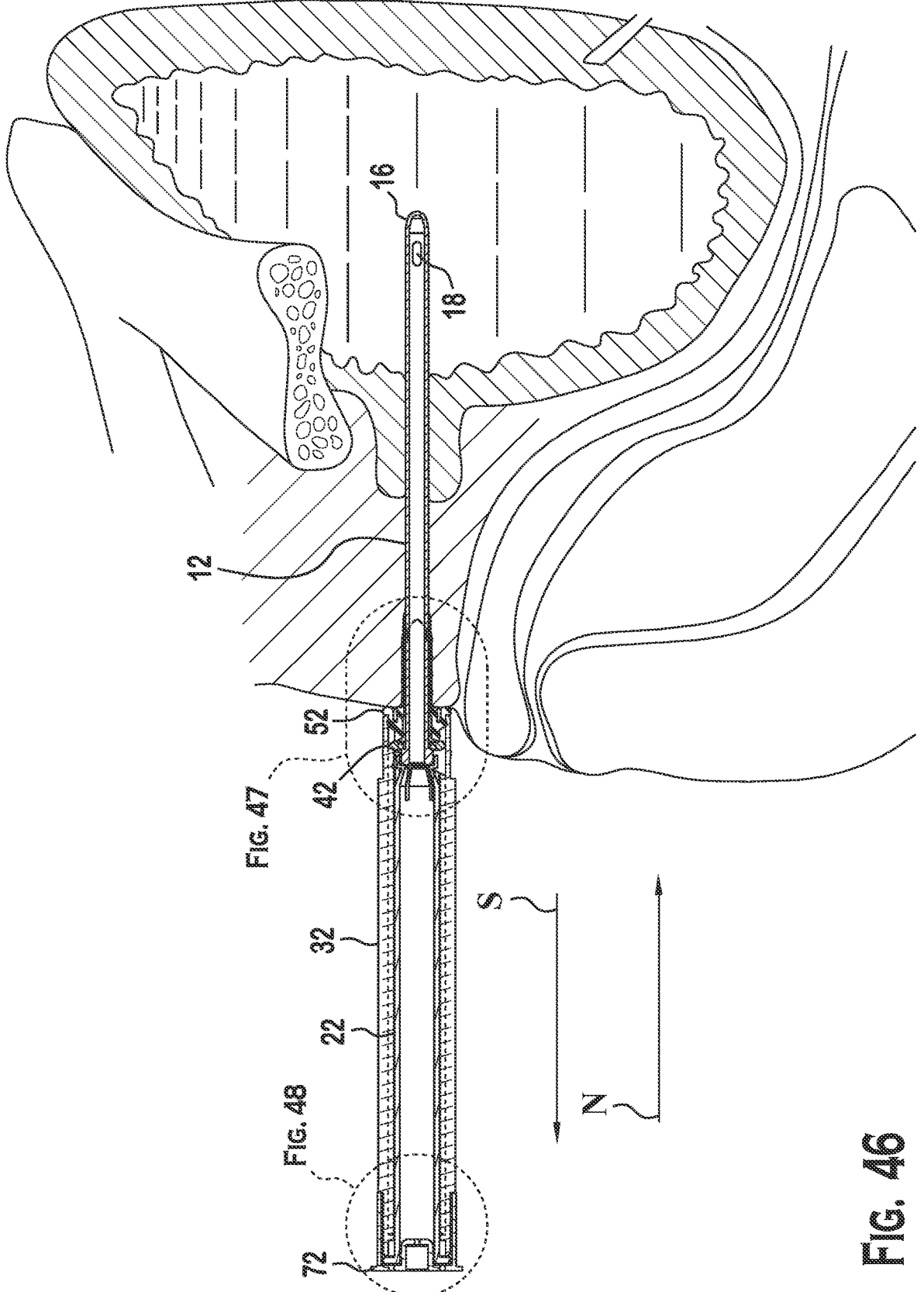
FIG. 46 is a perspective view of the invention of FIG. 45.
Figures 47, 48:
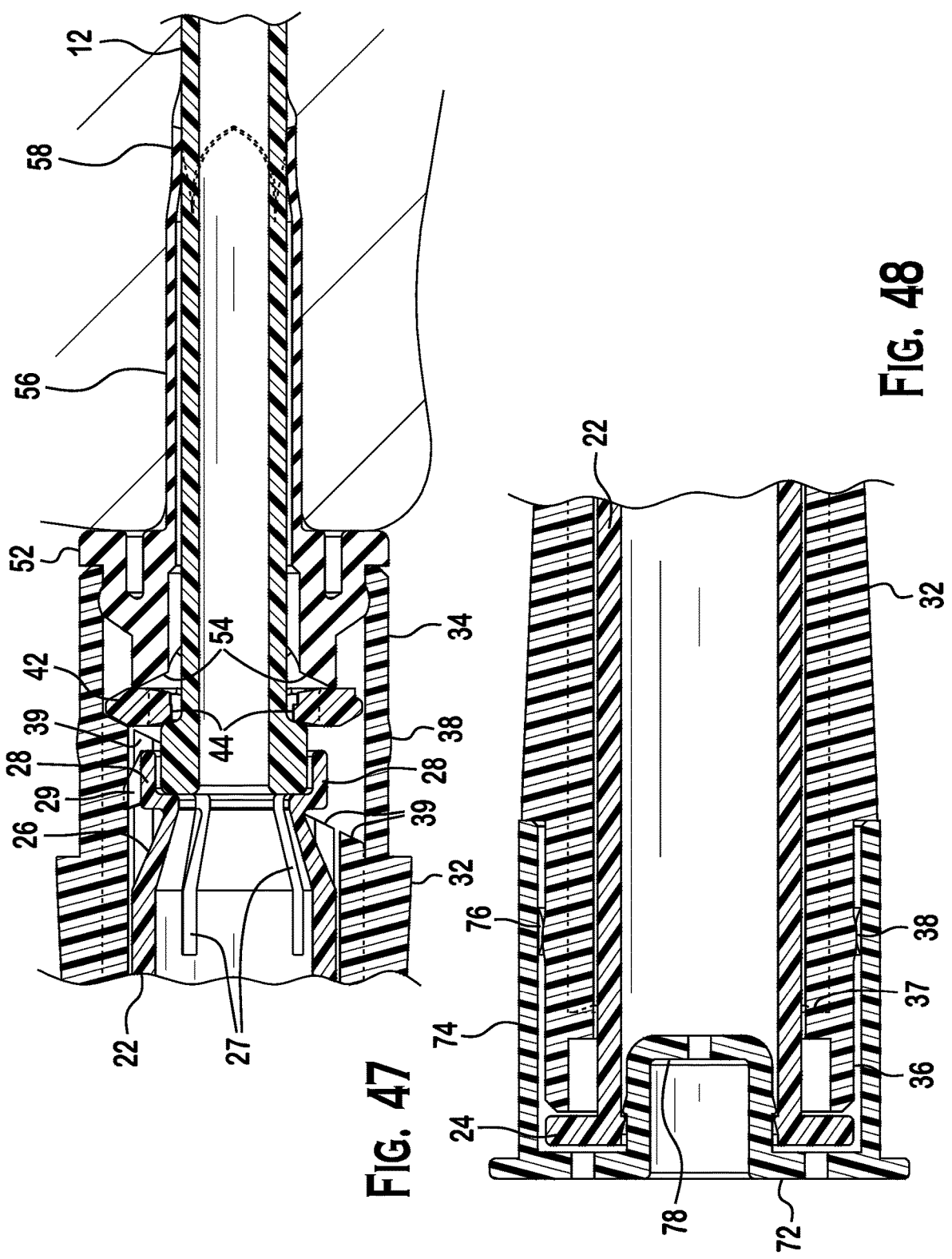
FIG. 47 is an enlarged view of the invention of FIG. 46.
FIG. 48 is another enlarged view of the invention of FIG. 47.

In the exemplary embodiment, as shown in FIGS. 26-28, the rear cap 70 is mainly composed of a rear cap base 72 and the rear cap body 74. One of ordinary skill in the art would understand the applicant's design is not the exclusive embodiment. The rear cap 70 further includes a front face 70a and a rear face 70b.

In the exemplary embodiment, the rear cap base 72 is a circular disk. The rear cap base 72 further includes a circular indent 78 located on the central region of the rear cap base 72 extending outwards from the front face 70a.

In the exemplary embodiment, the rear cap body 74 is cylindrical. One of ordinary skill in the art would understand the applicant's design is not the exclusive embodiment. In the exemplary embodiment, the rear cap body 74 further includes a cap raised groove 76 located on the inner portion of the rear cap body 74. One of ordinary skill in the art would understand the applicant's design is not the exclusive embodiment.

In the exemplary embodiment, the discrete catheter assembly 1 is generally constructed with the following major components: a containment unit and an outer protector layer.

As assembled, the catheter 10 is inserted into the holding vessel passageway 20c at holding base member 24 and extending the length of the holding vessel 20. One of ordinary skill in the art would understand the applicant's design is not the exclusive embodiment.

In the exemplary embodiment, the catheter 10 is inserted through the holding head member 26 and the retainer opening of the retainer 40. One of ordinary skill in the art would understand the applicant's design is not the exclusive embodiment. The combined components are inserted into the shell passageway 30c of the shell 30. The dispenser 50 is then positioned to the shell head 34. One of ordinary skill in the art would understand the applicant's design is not the exclusive embodiment.

In the exemplary embodiment, the catheter 10 is then inserted into the dispenser passageway 50c where the retainer 40 is positioned between the rear face 50b of the dispenser 50 and the holding head member 26. One of ordinary skill in the art would understand the applicant's design is not the exclusive embodiment.

In the exemplary embodiment, the rear cap 70 is fitted over the shell base 36 in, which the cap raised groove 76 is adjacent to the raised groove 38 of the shell base 36. One of ordinary skill in the art would understand the applicant's design is not the exclusive embodiment. Lastly, the front cap 60 is inserted over the dispenser 50 and secured to the shell head 34 by the raised groove 38 of the shell head 34.

When the assembly is ready to be used, the front cap 60 is removed allowing the dispenser 50 and specifically the distal tip 58 to be exposed.

In a neutral state, the retainer 40 is angled and is not in contact with the biasing surface 54, which allows for the catheter 10 to freely move in a first direction S as shown in FIGS. 29-35.

In an active state, the rear cap 70 is pulled in the first direction S extending the holding vessel 20 towards the shell base 36 of the shell 30. The flaps 29 of the holding vessel 20 engage and become flush with the plurality of rectangular protrusions 39 using the edge L, which allows the holding vessel 20 to glide and move freely.

The holding head member 26 makes contact with and becomes flush to an outer rim of the projecting base 14 of the catheter 10. The holding head member 26 continues to move as it passes over the projecting base 14 of the catheter 10 in the first direction S until the holding head member 26 is stopped by the free-floating circular ring 37 located on the inner face 30b of the shell base 36. Once the holding head member 26 has been stopped by the free-floating circular ring 37, the holding vessel 20 is fully extended as shown in FIGS. 37-44.

The rear cap 70 is then pushed in a second direction N where the circular cradle 28 makes contact with and nestles a rear of the projecting base 14 of the catheter 10 while continuing to move in the second direction N until the projecting base 14 makes contact with the retainer 40 as shown in FIGS. 45-48.

The retainer 40 is then angled perpendicular to the assembly. Further, the first face 40a of the retainer 40 is in contact and flush against the biasing surface 54 to maintain stability of the catheter 10 while a fluid is received. The catheter 10 travels through the dispenser passageway 50c and penetrates the distal tip 58 of the dispenser 50.

Figures 49, 50:
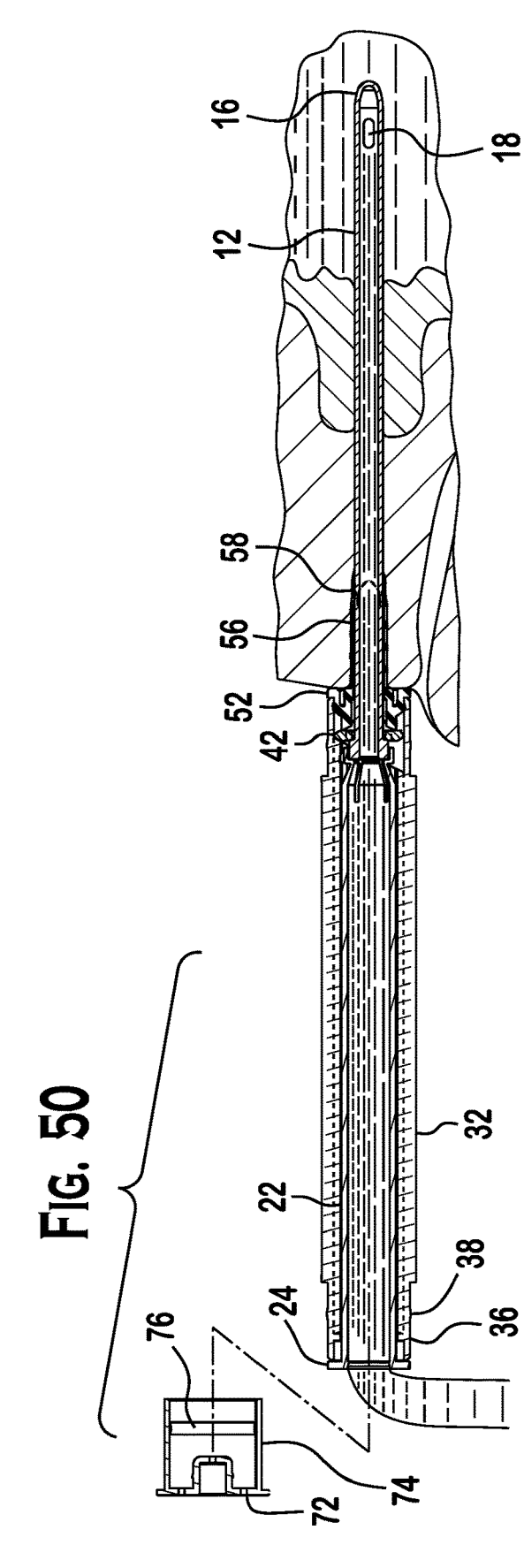
FIG. 49 a top, rear, right view of the invention of FIG. 48.
FIG. 50 is a sectional view of the invention of FIG. 49.

The fluid is then received through the eye slits 18 of the catheter 10. The fluid travels through the tube passageway and exits the catheter 10 through the projecting base 14 and into the holding vessel 20. The assembly 1 permits fluid communication between the distal and proximal ends and allows the fluid to be released and drained when the rear cap 70 is removed as shown in FIGS. 49-50.

In an alternative embodiment, a bag (not shown) may be attached to the shell base 36 in order for the fluid to drain into the bag. One of ordinary skill in the would understand the applicant's design is not the exclusive embodiment.

The foregoing illustrates some of the possibilities for practicing the invention. Many other embodiments are possible within the scope and spirit of the invention. It is, therefore, intended that the foregoing description be regarded as illustrative rather than limiting, and that the scope of the invention is given by the appended claims together with their full range of equivalents.

What is claimed is:

1. A discrete catheter assembly comprising:
a containment unit having:
    a holding vessel with a holding head member; and
    a catheter resting in an inner portion of the holding vessel and having a tube head positioned near the holding head member; and an outer protector layer having:
    a retainer having a first face and a second face;
    a dispenser positioned adjacent to the first face of the retainer;
    a shell enclosing the holding vessel and having a shell head, a shell base, and a plurality of rectangular protrusions extending a length of the shell;
    a front cap fitted over the shell head; and
    a rear cap fitted over the shell base in which the front cap is removed while the rear cap is moved in a first direction away from the dispenser, then moved in a second direction to permit movement of the catheter towards the dispenser.

2. The discrete catheter assembly of claim 1, wherein the dispenser includes a distal tip in which the catheter penetrates.

3. The discrete catheter assembly of claim 2, wherein the rear cap is removable and opens up to allow for fluid communication between a distal end and a proximal end of the containment unit.

4. The discrete catheter assembly of claim 3, wherein the holding vessel includes a holding base member at an opposite end from the holding head member.

5. The discrete catheter assembly of claim 4, wherein the holding vessel further includes a holding body member in between the holding base member and the holding head member.

6. The discrete catheter assembly of claim 5, wherein the catheter further includes a projecting base opposite of the tube head.

7. The discrete catheter assembly of claim 6, wherein the catheter further includes a tube body positioned between the projecting base and the tube head.

8. The discrete catheter assembly of claim 7, wherein the catheter further includes at least one eye slit positioned near the tube head.

9. The discrete catheter assembly of claim 8, wherein the retainer is a ring member.

10. The discrete catheter assembly of claim 9, wherein the retainer further includes a plurality of teeth like-protrusions positioned on an inner perimeter of the ring member.

11. The discrete catheter assembly of claim 10, wherein the retainer further includes a plurality of circular protrusions positioned parallel to the plurality of teeth like-protrusions.

12. The discrete catheter assembly of claim 11, wherein the retainer further includes a plurality of retainer indentations positioned between the plurality of teeth like-protrusions.

13. The discrete catheter assembly of claim 12, wherein the rectangular protrusions and the shell form an edge.

14. The discrete catheter assembly of claim 13, wherein a plurality of flaps engages with the rectangular protrusions of the shell.

15. The discrete catheter assembly of claim 14, wherein the holding head member is flush to an outer rim of the projecting base.

16. The discrete catheter assembly of claim 15, wherein the holding head member makes contact with a free floating ring in the first direction to prevent further movement.

17. The discrete catheter assembly of claim 16, wherein a circular cradle of the holding vessel makes contact with a rear of the projecting base in the second direction.

18. The discrete catheter assembly of claim 17, wherein the circular cradle and the projecting base move in unison in the second direction.

19. The discrete catheter assembly of claim 18, wherein the circular cradle and the projecting base make contact with the retainer in the second direction to prevent further movement.

* * * * *